(12) United States Patent
Viswanathan

(10) Patent No.: US 11,589,921 B2
(45) Date of Patent: *Feb. 28, 2023

(54) SYSTEMS, APPARATUSES AND METHODS FOR DELIVERY OF ABLATIVE ENERGY TO TISSUE

(71) Applicant: Boston Scientific Scimed, Inc., Maple Grove, MN (US)

(72) Inventor: Raju Viswanathan, Mountain View, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 251 days.

This patent is subject to a terminal disclaimer.

(21) Appl. No.: 16/921,654

(22) Filed: Jul. 6, 2020

(65) Prior Publication Data

US 2021/0121230 A1 Apr. 29, 2021

Related U.S. Application Data

(63) Continuation of application No. 16/723,407, filed on Dec. 20, 2019, now Pat. No. 10,709,502, and a
(Continued)

(51) Int. Cl.
*A61B 18/14* (2006.01)
*A61B 18/00* (2006.01)

(52) U.S. Cl.
CPC .............. *A61B 18/1492* (2013.01); *A61B 2018/00351* (2013.01); *A61B 2018/00577* (2013.01);
(Continued)

(58) Field of Classification Search
CPC ...... A61B 18/1492; A61B 2018/00351; A61B 2018/00375; A61B 2018/00577;
(Continued)

(56) References Cited

U.S. PATENT DOCUMENTS 3,683,923 A 8/1972 Anderson
4,092,986 A 6/1978 Schneiderman
(Continued)

FOREIGN PATENT DOCUMENTS

CN 105209117 A 12/2015
CN 105283143 A 1/2016
(Continued)

OTHER PUBLICATIONS

First Office Action for Chinese Application No. 201680077941.2, dated Jun. 30, 2020, 13 pages.
(Continued)

*Primary Examiner* — Khadijeh A Vahdat
(74) *Attorney, Agent, or Firm* — Nelson Mullins Riley & Scarborough LLP

(57) ABSTRACT

A system includes a pulse waveform generator and an ablation device coupled to the pulse waveform generator. The ablation device includes at least one electrode configured for ablation pulse delivery to tissue during use. The pulse waveform generator is configured to deliver voltage pulses to the ablation device in the form of a pulsed waveform. The pulsed waveform can include multiple levels of hierarchy, and multiple sets of electrodes can be activated such that their pulsed delivery is interleaved with one another.

28 Claims, 14 Drawing Sheets

Related U.S. Application Data continuation-in-part of application No. 16/722,650, filed on Dec. 20, 2019, now Pat. No. 10,709,891, which is a continuation of application No. 16/416,677, filed on May 20, 2019, now Pat. No. 10,512,779, said application No. 16/723,407 is a continuation of application No. 16/405,515, filed on May 7, 2019, now Pat. No. 10,512,505, said application No. 16/416,677 is a continuation of application No. 15/796,375, filed on Oct. 27, 2017, now Pat. No. 10,322,286, which is a continuation of application No. 15/334,646, filed on Oct. 26, 2016, now abandoned, which is a continuation of application No. PCT/US2016/057664, filed on Oct. 19, 2016.

(60) Provisional application No. 62/733,968, filed on Sep. 20, 2018, provisional application No. 62/667,950, filed on May 7, 2018, provisional application No. 62/274,926, filed on Jan. 5, 2016.

(52) U.S. Cl.
CPC ............... *A61B 2018/00767* (2013.01); *A61B 2018/1467* (2013.01)

(58) Field of Classification Search
CPC ........... A61B 2018/00613; A61B 2018/00767; A61B 2018/126; A61B 2018/1407; A61B 2018/1467
See application file for complete search history.

(56) References Cited

U.S. PATENT DOCUMENTS

| | | |
|---|---|---|
| 4,200,104 A | 4/1980 | Harris |
| 4,429,694 A | 2/1984 | McGreevy |
| 4,438,766 A | 3/1984 | Bowers |
| 4,470,407 A | 9/1984 | Hussein |
| 4,739,759 A | 4/1988 | Rexroth et al. |
| 4,919,508 A | 4/1990 | Grace et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,293,868 A | 3/1994 | Nardella |
| 5,304,214 A | 4/1994 | DeFord et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett, III et al. |
| 5,531,685 A | 7/1996 | Hemmer et al. |
| 5,545,161 A | 8/1996 | Imran |
| 5,558,091 A | 9/1996 | Acker et al. |
| 5,578,040 A | 11/1996 | Smith |
| 5,617,854 A | 4/1997 | Munsif |
| 5,624,430 A | 4/1997 | Eton et al. |
| 5,662,108 A | 9/1997 | Budd et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman et al. |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |

(56) References Cited

U.S. PATENT DOCUMENTS

| | | |
|---|---|---|
| 6,807,447 B2 | 10/2004 | Griffin, III |
| 6,810,241 B1 | 10/2004 | Salib |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,010,186 B1 | 8/2011 | Ryu et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |

(56) References Cited

U.S. PATENT DOCUMENTS

| | | |
|---|---|---|
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,788,885 B2 | 10/2017 | Long et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,117,701 B2 | 11/2018 | Davalos et al. |
| 10,117,707 B2 | 11/2018 | Garcia et al. |
| 10,130,423 B1 | 11/2018 | Viswanathan et al. |
| 10,172,673 B2 | 1/2019 | Viswanathan et al. |
| 10,292,755 B2 | 5/2019 | Arena et al. |
| 10,322,286 B2 | 6/2019 | Viswanathan et al. |
| 10,342,598 B2 | 7/2019 | Long et al. |
| 10,433,906 B2 | 10/2019 | Mickelsen |
| 10,433,908 B2 | 10/2019 | Viswanathan et al. |
| 10,448,989 B2 | 10/2019 | Arena et al. |
| 10,507,302 B2 | 12/2019 | Leefl et al. |
| 10,512,505 B2 | 12/2019 | Viswanathan |
| 10,512,779 B2 | 12/2019 | Viswanathan et al. |
| 10,517,672 B2 | 12/2019 | Long |
| 10,531,914 B2 | 1/2020 | Stewart et al. |
| 10,625,080 B1 | 4/2020 | Viswanathan |
| 10,688,305 B1 | 6/2020 | Viswanathan |
| 10,709,502 B2 | 7/2020 | Viswanathan |
| 10,709,891 B2 | 7/2020 | Viswanathan et al. |
| 10,842,572 B1 | 11/2020 | Viswanathan |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Liddicoat et al. |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0078494 A1 | 4/2003 | Panescu et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek-Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0147920 A1 | 7/2004 | Keidar |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Chrisitian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0091970 A1 | 5/2006 | Mondal |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0134273 A1 | 6/2010 | Weiss et al. |

(56) References Cited

U.S. PATENT DOCUMENTS

| | | |
|---|---|---|
| 2010/0135550 A1 | 6/2010 | Arnon |
| 2010/0137861 A1 | 6/2010 | Soroff et al. |
| 2010/0168550 A1 | 7/2010 | Byrd et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0015628 A1 | 1/2011 | Dalal et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0098699 A1 | 4/2011 | Pachon et al. |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0202051 A1 | 8/2011 | Hagg et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0109242 A1 | 5/2012 | Levin et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0135748 A1 | 5/2014 | Dai et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0257144 A1 | 9/2014 | Capelli et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2014/0378958 A1 | 12/2014 | Leussler |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0080693 A1 | 3/2015 | Solis |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0141982 A1 | 5/2015 | Lee |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0223902 A1 | 8/2015 | Walker et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |

(56) References Cited

U.S. PATENT DOCUMENTS

| | | |
|---|---|---|
| 2015/0321021 A1 | 11/2015 | Tandri et al. |
| 2015/0327944 A1 | 11/2015 | Neal, II et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0338770 A1 | 11/2016 | Bar-Tal et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0120048 A1 | 5/2017 | He et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0056073 A1 | 3/2018 | Torgerson |
| 2018/0064488 A1 | 3/2018 | Long et al. |
| 2018/0078170 A1 | 3/2018 | Panescu et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0145595 A1 | 5/2018 | Fontana et al. |
| 2018/0168511 A1 | 6/2018 | Hall et al. |
| 2018/0184982 A1 | 7/2018 | Basu et al. |
| 2018/0193090 A1 | 7/2018 | de la Rama et al. |
| 2018/0200497 A1 | 7/2018 | Mickelsen |
| 2018/0214195 A1 | 8/2018 | Fraasch et al. |
| 2018/0214202 A1 | 8/2018 | Howard et al. |
| 2018/0221078 A1 | 8/2018 | Howard et al. |
| 2018/0221085 A1 | 8/2018 | Blanck et al. |
| 2018/0235496 A1 | 8/2018 | Wu et al. |
| 2018/0243558 A1 | 8/2018 | Athos et al. |
| 2018/0250508 A1 | 9/2018 | Howard |
| 2018/0280080 A1 | 10/2018 | Govari et al. |
| 2018/0289417 A1 | 10/2018 | Schweitzer et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344202 A1 | 12/2018 | Bar-Tal et al. |
| 2018/0344393 A1 | 12/2018 | Gruba et al. |
| 2018/0360531 A1 | 12/2018 | Holmes et al. |
| 2018/0360534 A1 | 12/2018 | Teplitsky et al. |
| 2019/0015007 A1 | 1/2019 | Rottmann et al. |
| 2019/0030328 A1 | 1/2019 | Stewart et al. |
| 2019/0038171 A1 | 2/2019 | Howard |
| 2019/0060632 A1 | 2/2019 | Asirvatham et al. |
| 2019/0069950 A1 | 3/2019 | Viswanathan et al. |
| 2019/0125439 A1 | 5/2019 | Rohl et al. |
| 2019/0151015 A1 | 5/2019 | Viswanathan et al. |
| 2019/0175263 A1 | 6/2019 | Altmann et al. |
| 2019/0183378 A1 | 6/2019 | Mosesov et al. |
| 2019/0183567 A1 | 6/2019 | Govari et al. |
| 2019/0192223 A1 | 6/2019 | Rankin |
| 2019/0201089 A1 | 7/2019 | Waldstreicher et al. |
| 2019/0209238 A1 | 7/2019 | Jimenez |
| 2019/0223938 A1 | 7/2019 | Arena et al. |
| 2019/0223948 A1 | 7/2019 | Stewart et al. |
| 2019/0223950 A1 | 7/2019 | Gelbart et al. |
| 2019/0231421 A1 | 8/2019 | Viswanathan et al. |
| 2019/0231425 A1 | 8/2019 | Waldstreicher et al. |
| 2019/0233809 A1 | 8/2019 | Neal, II et al. |
| 2019/0256839 A1 | 8/2019 | Neal, II et al. |
| 2019/0269912 A1 | 9/2019 | Viswanathan et al. |
| 2019/0328445 A1 | 10/2019 | Sano et al. |
| 2019/0336198 A1 | 11/2019 | Viswanathan et al. |
| 2019/0336207 A1 | 11/2019 | Viswanathan |
| 2019/0350647 A1 | 11/2019 | Ramberg et al. |
| 2019/0350649 A1 | 11/2019 | Sutermeister et al. |
| 2019/0376055 A1 | 12/2019 | Davalos et al. |
| 2020/0107879 A1 | 4/2020 | Stewart et al. |
| 2020/0129233 A1 | 4/2020 | Viswanathan et al. |
| 2020/0139114 A1 | 5/2020 | Viswanathan et al. |
| 2020/0230403 A1 | 7/2020 | Bowers |
| 2021/0022794 A1 | 1/2021 | Viswanathan |

FOREIGN PATENT DOCUMENTS

| | | |
|---|---|---|
| CN | 106388932 A | 2/2017 |
| CN | 107921258 A | 4/2018 |
| EP | 1042990 A1 | 10/2000 |
| EP | 1125549 | 8/2001 |
| EP | 0797956 | 6/2003 |
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |

(56) References Cited

FOREIGN PATENT DOCUMENTS

| | | |
|---|---|---|
| EP | 2708181 | 3/2014 |
| EP | 2777579 A1 | 9/2014 |
| EP | 2934307 | 10/2015 |
| EP | 2777585 | 6/2016 |
| EP | 2382935 B1 | 3/2018 |
| EP | 3111871 B1 | 3/2018 |
| EP | 3151773 B1 | 4/2018 |
| EP | 3056242 B1 | 7/2018 |
| JP | H06-507797 | 9/1994 |
| JP | H10-510745 | 10/1998 |
| JP | 2000-508196 | 7/2000 |
| JP | 2005-516666 | 6/2005 |
| JP | 2006-506184 | 2/2006 |
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| JP | 2015-524732 | 8/2015 |
| JP | 2015-532604 | 11/2015 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2008/035070 | 3/2008 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/093926 | 6/2017 |
| WO | WO 2017/119934 | 7/2017 |
| WO | WO 2017/120169 | 7/2017 |
| WO | 2017/201504 A1 | 11/2017 |
| WO | WO 2017/192477 | 11/2017 |
| WO | WO 2017/192495 | 11/2017 |
| WO | WO 2017/218734 | 12/2017 |
| WO | 2018/010659 A1 | 1/2018 |
| WO | WO 2018/005511 | 1/2018 |
| WO | WO 2018/200800 | 11/2018 |
| WO | WO 2018/208795 | 11/2018 |
| WO | WO 2019/118436 | 6/2019 |
| WO | WO 2019/133606 | 7/2019 |
| WO | WO 2019/133608 | 7/2019 |
| WO | WO 2019/147832 | 8/2019 |
| WO | WO 2019/152986 | 8/2019 |
| WO | WO 2019/173309 | 9/2019 |

OTHER PUBLICATIONS

Extended European Search Report for European Application No. 16884132.8, dated Jul. 8, 2019, 7 pages.
Notice of Reasons for Rejection for Japanese Application No. 2018-534869, dated Jul. 29, 2020, 11 pages.
Office Action for U.S. Appl. No. 15/334,646, dated Jul. 25, 2017, 19 pages.
Office Action for U.S. Appl. No. 15/334,646, dated Nov. 16, 2017, 26 pages.
International Search Report and Written Opinion for International Application No. PCT/US2016/057664, dated Feb. 24, 2017, 11 pages.
Office Action for U.S. Appl. No. 15/796,375, dated Jan. 24, 2018, 25 pages.
Office Action for U.S. Appl. No. 15/796,375, dated May 30, 2018, 26 pages.
Office Action for U.S. Appl. No. 15/796,375, dated Nov. 16, 2018, 27 pages.
Office Action for U.S. Appl. No. 16/416,677, dated Aug. 15, 2019, 8 pages.
Office Action for U.S. Appl. No. 16/722,650, dated Mar. 25, 2020, 12 pages.
Office Action for U.S. Appl. No. 15/499,804, dated Jan. 3, 2018, 20 pages.
Office Action for U.S. Appl. No. 15/794,717, dated Feb. 1, 2018, 10 pages.
International Search Report and Written Opinion for International Application No. PCT/US2018/029552, dated Jun. 29, 2018, 13 pages.
International Search Report and Written Opinion for International Application No. PCT/US2019/017322, dated May 10, 2019, 15 pages.
International Search Report and Written Opinion for International Application No. PCT/US2019/030922, dated Sep. 6, 2019, 12 pages.
Office Action for U.S. Appl. No. 16/573,704, dated Dec. 17, 2019, 6 pages.
Office Action for U.S. Appl. No. 16/741,506, dated Feb. 28, 2020, 5 pages.
Office Action for U.S. Appl. No. 16/689,967, dated Jul. 22, 2020, 23 pages.
Office Action for U.S. Appl. No. 16/405,515, dated Sep. 6, 2019, 9 pages.
International Search Report and Written Opinion for International Application No. PCT/US2019/031135, dated Aug. 5, 2019, 11 pages.
Office Action for U.S. Appl. No. 16/723,407, dated Mar. 19, 2020, 13 pages.
Office Action for U.S. Appl. No. 16/785,392, dated May 29, 2020, 18 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).

(56) References Cited

OTHER PUBLICATIONS

Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Tekle, E. et al., "Electroporation by using bipolar oscillating electric field: An improved method for DNA transfection of NIH 3T3 cells," Proc. Natl. Acad. Sci. USA, vol. 88, pp. 4230-4234, May 1991.
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Office Action for U.S. Appl. No. 17/091,289, dated Jan. 26, 2021, 18 pages.
International Search Report and Written Opinion for International Application No. PCT/US2020/051272, dated Jan. 22, 2021, 10 pages.
Office Action for U.S. Appl. No. 16/689,967, dated Dec. 22, 2020, 16 pages.

SYSTEMS, APPARATUSES AND METHODS FOR DELIVERY OF ABLATIVE ENERGY TO TISSUE

CROSS-REFERENCE TO RELATED APPLICATIONS

The application is a continuation of U.S. application Ser. No. 16/723,407, filed Dec. 20, 2019, titled "SYSTEMS, APPARATUSES AND METHODS FOR DELIVERY OF ABLATIVE ENERGY TO TISSUE", and now issued as U.S. Pat. No. 10,709,502, which is a continuation of U.S. application Ser. No. 16/405,515, filed May 7, 2019, titled "SYSTEMS, APPARATUSES AND METHODS FOR DELIVERY OF ABLATIVE ENERGY TO TISSUE", and now issued as U.S. Pat. No. 10,512,505, which claims the benefit of U.S. Provisional Application Ser. No. 62/733,968, filed on Sep. 20, 2018, titled "SYSTEMS, APPARATUSES AND METHODS FOR DELIVERY OF ABLATIVE ENERGY TO TISSUE", and U.S. Provisional Application Ser. No. 62/667,950, filed on May 7, 2018, titled "SYSTEMS, APPARATUSES AND METHODS FOR DELIVERY OF ABLATIVE ENERGY TO TISSUE". This application is also a continuation-in-part of U.S. patent application Ser. No. 16/722,650, filed Dec. 20, 2019, titled "SYSTEMS, APPARATUSES AND METHODS FOR DELIVERY OF ABLATIVE ENERGY TO TISSUE", and now issued as U.S. Pat. No. 10,709,891, which is a continuation of U.S. patent application Ser. No. 16/416,677, filed May 20, 2019, titled "SYSTEMS, APPARATUSES AND METHODS FOR DELIVERY OF ABLATIVE ENERGY TO TISSUE", and now issued as U.S. Pat. No. 10,512,779, which is a continuation of U.S. patent application Ser. No. 15/796,375, filed Oct. 27, 2017, titled "SYSTEMS, APPARATUSES AND METHODS FOR DELIVERY OF ABLATIVE ENERGY TO TISSUE", and now issued as U.S. Pat. No. 10,322,286, which is a continuation of U.S. patent application Ser. No. 15/334,646, titled "SYSTEMS, APPARATUSES AND METHODS FOR DELIVERY OF ABLATIVE ENERGY TO TISSUE", filed Oct. 26, 2016, which is a continuation of PCT Application No. PCT/US2016/057664, titled "SYSTEMS, APPARATUSES AND METHODS FOR DELIVERY OF ABLATIVE ENERGY TO TISSUE", and filed Oct. 19, 2016, which claims priority to U.S. Provisional Application Ser. No. 62/274,926, titled "METHOD AND APPARATUS FOR DELIVERY OF PULSED ELECTRIC FIELD ABLATIVE ENERGY TO TISSUE", and filed Jan. 5, 2016. The entire disclosure of each of the foregoing applications is incorporated by reference in its entirety.

BACKGROUND

The generation of pulsed electric fields for tissue therapeutics has moved from the laboratory to clinical applications over the past two decades, while the effects of brief pulses of high voltages and large electric fields on tissue have been investigated for the past forty years or more. Application of brief high DC voltages to tissue, which can generate locally high electric fields typically in the range of hundreds of Volts/centimeter, can disrupt cell membranes by generating pores in the cell membrane. While the precise mechanism of this electrically-driven pore generation or electroporation is unclear, it is thought that the application of relatively large electric fields generates instabilities in the lipid bilayers in cell membranes, causing the occurrence of a distribution of local gaps or pores in the membrane. If the applied electric field at the membrane is larger than a threshold value, the electroporation can be irreversible and the pores remain open, permitting exchange of biomolecular material across the membrane and leading to necrosis and/or apoptosis (cell death). Subsequently the surrounding tissue heals in a natural process.

Hence, known electroporation applications in medicine and delivery methods do not address high voltage application, electrode sequencing, tissue selectivity, and safe energy delivery, especially in the context of ablation therapy for cardiac arrhythmias with catheter devices. Further, there is an unmet need for thin, flexible, atraumatic devices that can at the same time effectively deliver high DC voltage electroporation ablation therapy selectively to tissue in regions of interest while minimizing damage to healthy tissue, and for a combination of device design and dosing waveform that involves minimal or no device repositioning, permitting an effective, safe and rapid clinical procedure.

SUMMARY

Described here are systems, devices, and methods for ablating tissue through irreversible electroporation. In some embodiments, a system can include an ablation device including a plurality of electrodes configured to generate an electric field for ablating tissue in a subject, for example in cardiac anatomy. A pulse waveform generator may be couplable to the ablation device and configured to deliver voltage pulses to the ablation device in the form of a pulsed waveform. The pulsed waveform may include a first level of a hierarchy of the pulsed waveform that includes a first set of pulses and first time delays separating successive pulses of the first set of pulses, each pulse of the first set of pulses having a pulse time duration. A second level of the hierarchy may include a plurality of first sets of pulses as a second set of pulses and second time delays separating successive first sets of pulses of the plurality of first sets of pulses, each second time delay being at least three times the duration of a first time delay. A third level of the hierarchy may include a plurality of second sets of pulses as a third set of pulses and third time delays separating successive second sets of pulses of the plurality of second sets of pulses, each third time delay being at least thirty times the duration of a second time delay. A fourth level of the hierarchy may includes a plurality of third sets of pulses as a fourth set of pulses and fourth time delays separating successive third sets of pulses of the plurality of third sets of pulses, each fourth time delay being at least ten times the duration of a third time delay.

In some embodiments, each pulse of each first set of pulses includes biphasic pulses each with a voltage amplitude of at least 500 Volts, the pulse time duration of each biphasic pulse being in the range from about 0.5 nanosecond to about 20 microseconds. In some embodiments, the fourth set of pulses may include at least two third sets of pulses and less than forty third sets of pulses. In some embodiments, each fourth time delay may have a constant duration. In some embodiments, the fourth time delays vary in duration. In some of these embodiments, the fourth time delays include at least one repeating value of time delay. In some of these embodiments, each fourth time delay has a duration within a range extending from at least ten times the duration of a third time delay to less than one thousand times the duration of a third time delay. In some embodiments, each fourth time delay may be greater in duration than a cardiac cycle of the heart.

In some embodiments, the pulsed waveform further includes a fifth level of the hierarchy including a plurality of fourth sets of pulses as a fifth set of pulses and fifth time delays separating successive fourth sets of pulses of the plurality of fourth sets of pulses, each fifth time delay being at least ten times the duration of at least one of the fourth time intervals. In some embodiments, the pulse waveform generator may be configured to deliver the voltage pulses in the form of the pulsed waveform in synchrony with cardiac cycles of the heart such that successive second sets of pulses of the plurality of second sets of pulses are delivered during refractory periods of distinct cardiac cycles of the heart, and with a delivery window of the fourth set of pulses extending across a plurality of cardiac cycles of the heart. In some of these embodiments, each second set of pulses includes at least two first sets of pulses and less than forty first sets of pulses. In some of these embodiments, a cardiac stimulator may be configured to generate pacing signals for controlling timing of the cardiac cycles of the heart. In some embodiments, the pulse waveform generator may be further configured to deliver the voltage pulses to a plurality of electrode sets of the ablation device with voltage pulses delivered to a first electrode set being offset by a period of time from voltage pulses delivery to a second electrode set.

In some embodiments, a system may include an ablation device including a plurality of electrodes configured to generate an electric field for ablating tissue in a subject. A pulse waveform generator may be couplable to the ablation device. The pulse waveform generator may be configured to deliver voltage pulses in the form of a pulsed waveform to the ablation device by interleaving the voltage pulses being delivered across a plurality of electrode sets. The pulsed waveform may include a first level of a hierarchy of the pulsed waveform that includes a first set of pulses and first time delays separating successive pulses of the first set of pulses, each pulse of the first set of pulses having a pulse time duration. A second level of the hierarchy may include a plurality of first sets of pulses as a second set of pulses and second time delays separating successive first sets of pulses of the plurality of first sets of pulses, each second time delay being at least three times the duration of a first time delay. A third level of the hierarchy may include a plurality of second sets of pulses as a third set of pulses and third time delays separating successive second sets of pulses of the plurality of second sets of pulses, each third time delay being at least thirty times the duration of a second level time delay.

In some embodiments, each pulse of each first set of pulses includes biphasic pulses each with a voltage amplitude of at least 500 Volts, the pulse time duration of each biphasic pulse being in the range from about 0.5 nanosecond to about 20 microseconds.

In some embodiments, the pulse waveform generator may be configured to deliver the voltage pulses by delivering voltage pulses to a first electrode set of the plurality of electrode sets offset by a period of time from delivering voltage pulses to a second electrode set of the plurality of electrode sets. In some of these embodiments, the period of time offsetting the delivery of voltage pulses to the first electrode set and the delivery of voltage pulses to the second electrode set may be less than the duration of the second time delay, such that successive first sets of pulses delivered to the second electrode set follow successive first sets of pulses delivered to the first electrode set. In some of these embodiments, the period of time offsetting the delivery of voltage pulses to the first electrode set and the delivery of voltage pulses to the second electrode set may be less than about fifty five percent of the duration of the second time delay.

In some embodiments, the pulse waveform generator may be configured to deliver the voltage pulses in synchrony with cardiac cycles of the heart such that successive second sets of pulses of the plurality of second sets of pulses for a given electrode set are delivered during refractory periods of distinct cardiac cycles of the heart and the second sets of pulses delivered to at least two electrode sets of the plurality of electrode sets are delivered during a single refractory period. In some of these embodiments, a cardiac stimulator may be configured to generate pacing signals for controlling timing of the cardiac cycles of the heart.

In some embodiments, a method may include generating voltage pulses in the form of a pulsed waveform, the pulsed waveform including: a first level of a hierarchy of the pulsed waveform that includes a first set of pulses and first time delays separating successive pulses of the first set of pulses, each pulse of the first set of pulses having a pulse time duration; a second level of the hierarchy that includes a plurality of first sets of pulses as a second set of pulses and second time delays separating successive first sets of pulses of the plurality of first sets of pulses, each second time delay being at least three times the duration of a first time delay; a third level of the hierarchy includes a plurality of second sets of pulses as a third set of pulses and third time delays separating successive second sets of pulses of the plurality of second sets of pulses, each third time delay being at least thirty times the duration of a second level time delay; and a fourth level of the hierarchy that includes a plurality of third sets of pulses as a fourth set of pulses and fourth time delays separating successive third sets of pulses of the plurality of third sets of pulses, each fourth time delay being at least ten times the duration of a third time delay. The method can further include delivering the voltage pulses to one or more electrode sets of an ablation device, such that the one or more electrode sets generate a pulsed electric field for ablating tissue in a subject.

In some embodiments, the fourth set of pulses may include at least two third sets of pulses and less than forty third sets of pulses. In some embodiments, the fourth time delays may vary in duration with each fourth time delay having a duration within a range extending from at least ten times the duration of a third time delay to less than one thousand times the duration of a third time delay.

In some embodiments, the method may further comprise generating a set of pacing signals with a cardiac stimulator, and delivering the set of pacing signals to the heart. The voltage pulses may be delivered in synchrony with the set of pacing signals such that each second set of pulses of the plurality of second sets of pulses is delivered during a refractory period associated with each pacing signal of the set of pacing signals, and with a delivery window of the fourth set of pulses extending across a plurality of cardiac cycles of the heart.

In some of these embodiments, each fourth time delay may be greater in duration than a period of time separating success pacing signals from the set of pacing signals. In some embodiments, the pulsed waveform may further include a fifth level of the hierarchy including a plurality of fourth sets of pulses as a fifth set of pulses and fifth time delays separating successive fourth sets of pulses of the plurality of fourth sets of pulses, each fifth time delay being at least ten times the duration of at least one of the fourth time intervals.

In some embodiments, a method may include generating voltage pulses in the form of a pulsed waveform, the pulsed waveform including: a first level of a hierarchy of the pulsed waveform that includes a first set of pulses and first time delays separating successive pulses of the first set of pulses, each pulse of the first set of pulses having a pulse time duration; a second level of the hierarchy that includes a plurality of first sets of pulses as a second set of pulses and second time delays separating successive first sets of pulses of the plurality of first sets of pulses, each second time delay being at least three times the duration of a first time delay; and a third level of the hierarchy includes a plurality of second sets of pulses as a third set of pulses and third time delays separating successive second sets of pulses of the plurality of second sets of pulses, each third time delay being at least thirty times the duration of a second level time delay. The method may further include delivering the voltage pulses to a plurality of electrode sets of an ablation device by interleaving the voltage pulses delivered to at least two of the electrode sets of the plurality of electrode sets, such that the one or more electrode sets generate a pulsed electric field for ablating tissue in a subject.

In some embodiments, the voltage pulses may be delivered to a first electrode set of the at least two electrode sets offset by a period of time from delivering the voltage pulses to a second electrode set of the at least two electrode sets. In some embodiments, the period of time offsetting the delivery of voltage pulses to the first electrode set and the delivery of voltage pulses to the second electrode set may be less than about fifty five percent of the duration of the second time delay.

In some embodiments, the method may further comprise generating a set of pacing signals with a cardiac stimulator and delivering the set of pacing signals to a heart. The voltage pulses being delivered in synchrony with the set of pacing signals may be such that each second set of pulses of the plurality of second sets of pulses is delivered during a refractory period associated with a distinct pacing signal of the set of pacing signals and the second sets of pulses delivered to at least two electrode sets of the plurality of electrode sets may be delivered during a single refractory period.

DETAILED DESCRIPTION

Figure 1:
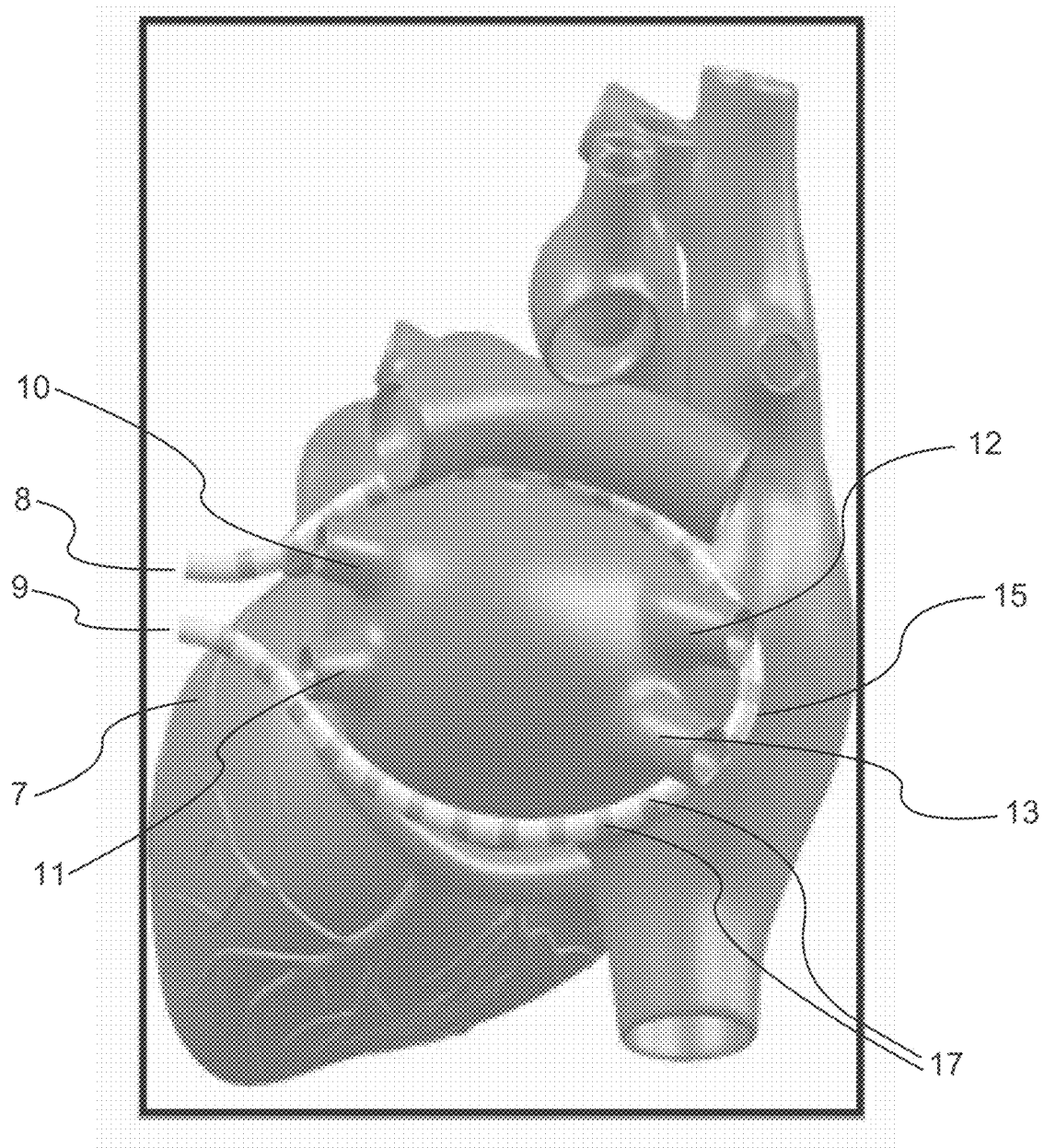
FIG. 1 is a schematic illustration of a catheter with a plurality of electrodes disposed along its distal shaft, epicardially disposed such that it snugly wraps around the pulmonary veins of a cardiac anatomy, according to embodiments.

Described here are systems, devices, and methods for ablating tissue through irreversible electroporation. Generally, a system for delivering a pulse waveform to tissue may include a pulse waveform generator and an ablation device coupled to the pulse waveform generator. The ablation device may include at least two electrodes configured for ablation pulse delivery to tissue during use. The pulse waveform generator may be configured to deliver voltage pulses to the ablation device in the form of a pulsed waveform.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may comprise one or more of the methods, systems, and devices described in one or more of the above-referenced and incorporated International Application Serial No. PCT/US2016/057664, filed on Oct. 19, 2016, U.S. patent application Ser. No. 15/334,646, filed on Oct. 26, 2016, and U.S. patent application Ser. No. 15/796,375, filed on Oct. 27, 2017.

In some embodiments, a system includes a pulse waveform generator and an ablation device coupled to the pulse waveform generator. The ablation device includes at least one electrode configured for ablation pulse delivery to tissue during use. The pulse waveform generator is configured to deliver voltage pulses to the ablation device in the form of a pulsed waveform. A first level of a hierarchy of the pulsed waveform applied to a given electrode includes a first set of pulses, each pulse having a pulse time duration and a first time interval (i.e., first time delay) separating successive pulses. A second level of the hierarchy of the pulsed waveform includes a plurality of first sets of pulses as a second set of pulses and a second time interval (i.e., second time delay) separating successive first sets of pulses, the second time interval being at least three times the duration of the first time interval. A third level of the hierarchy of the pulsed waveform includes a plurality of second sets of pulses as a third set of pulses and a third time interval (i.e., third time delay) separating successive second sets of pulses, the third time interval being at least 30 times the duration of the second time interval. A fourth level of the hierarchy of the pulsed waveform includes a plurality of third sets of pulses as a fourth set of pulses and a fourth time interval (i.e., a fourth time delay) separating successive third sets of pulses, the fourth time interval being at least ten times the duration of the third time interval.

In some embodiments, the pulses of each first set of pulses include monophasic pulses with a pulse time duration in the range from about 1 microsecond to about 300 microseconds. In some embodiments, the pulses of each first set of pulses include biphasic pulses each with a pulse time duration in the range from about 0.5 nanosecond to about 20 microseconds. In some embodiments, the second time interval is at least ten times the pulse time duration. In some embodiments, the third time interval is in the range of about hundreds of milliseconds or tenths of a second. In some embodiments, the fourth time interval is in the range from about seconds to about minutes. In some embodiments, the fourth time interval can vary or be non-constant over a series of third sets of pulses. In some embodiments, the fourth time interval can include at last one repeating value of time delay.

In some embodiments, each second set of pulses includes at least 2 first sets of pulses and less than 40 first sets of pulses. In some embodiments, each third set of pulses includes at least 2 second sets of pulses and less than 30 second sets of pulses. In some embodiments, each fourth set of pulses includes at least two third sets of pulses and less than forty third sets of pulses.

In some embodiments, the pulse waveform includes a fifth level of the hierarchy that includes a plurality of fourth sets of pulses as a fifth set of pulses, and a fifth time interval separating successive fourth sets of pulses. In some embodiments, each fifth set of pulses includes at least one fourth set of pulses to about 50 fourth sets of pulses.

Delivery of electroporation energy using a sequenced set of electrode pairings may increase the efficiency and/or speed with which the energy is delivered during a heartbeat. This may be useful in completing delivery of ablation energy within a predetermined time period (e.g., within a heartbeat, a refractory window of a cardiac chamber, and/or the like). For example, ablation delivery may be completed in time windows of less than about 100 ms, less than about 150 ms, less than about 200 ms, and less than about 250 ms in various embodiments.

In some embodiments, ablation energy delivery may be implemented as a sequential delivery of pulses using different sets of electrode pairings over a predetermined number of successive or distinct heartbeats. In particular, ablation delivery may be sequenced using a set of electrode pairings. For example, one or more groups of pulses may be delivered with a group delay between successive groups of pulses for each electrode pairing in a sequence of electrode pairings. In some of these embodiments, each electrode pairing may include a set of anodes paired with a set of cathodes. In this manner, energy delivery may be interleaved across a plurality of sets of electrode pairings during one or more heartbeats. During the group delay associated with a first set of paired electrodes, one or more groups of pulses may be delivered using a second set of paired electrodes.

In some embodiments, a first level of a hierarchy of the pulsed waveform applied to a given electrode may include a first set of pulses, each pulse having a pulse time duration, and a first time interval separating successive pulses. A second level of the hierarchy of the pulsed waveform may include a plurality of first sets of pulses as a second set of pulses, and a second time interval separating successive first sets of pulses. The second time interval may be at least three times the duration of the first time interval. A third level of the hierarchy of the pulsed waveform may include a plurality of second sets of pulses as a third set of pulses. A third time interval may separate successive second sets of pulses. The third time interval may be at least thirty times the duration of the second time interval. A fourth level of the hierarchy of the pulsed waveform may include a plurality of third sets of pulses as a fourth set of pulses. A fourth time interval may separate successive fourth sets of pulses. The fourth time interval may be at least ten times the duration of the third time interval.

Pulsed waveforms for electroporation energy delivery as disclosed herein can enhance the safety, efficiency and effectiveness of the energy delivery by reducing the electric field threshold associated with irreversible electroporation, yielding more effective ablative lesions with reduced total energy delivered. This in turn can broaden the areas of clinical application of electroporation including therapeutic treatment of a variety of cardiac arrhythmias.

The present disclosure addresses the need for devices and methods for rapid, selective and safe delivery of irreversible electroporation therapy, generally with multiple devices, such that, in some embodiments, peak electric field values can be reduced and/or minimized while at the same time sufficiently large electric field magnitudes can be maintained in regions where tissue ablation is desired. This also reduces the likelihood of excessive tissue damage or the generation of electrical arcing, and locally high temperature increases.

The terms "about" and "approximately" as used herein in connection with a referenced numeric indication means the referenced numeric indication plus or minus up to 10% of that referenced numeric indication. For example, the language "about 50" units or "approximately 50" units means from 45 units to 55 units. The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Overview

FIG. 1 is a schematic illustration of a catheter 15 with a plurality of electrodes disposed along its shaft. The catheter is shown in FIG. 1 in relation to a heart 7 and the catheter 15 is wrapped epicardially around the pulmonary veins of the left atrium denoted by reference characters 10, 11, 12 and 13 (respectively Left Superior, Left Inferior, Right Superior and Right Inferior in FIG. 1) and has electrodes indicated by dark bands (such as those denoted by reference character 17 in FIG. 1) that are wrapped and/or looped in a contour around the pulmonary veins 10, 11, 12, 13 of the left atrium. In some embodiment, catheter ends 8 and 9 are tightly drawn together and held inside a cinching tool (not shown) in order to ensure that the catheter electrodes are snugly wrapped around the pulmonary veins 10, 11, 12, 13. A method and apparatus using a subxiphoid pericardial access location and a guidewire-based delivery method to accomplish the placement of a multi-electrode ablation catheter around the pulmonary veins was described in PCT Patent Application Publication No. WO2014/025394, entitled "Catheters, Catheter Systems and Methods for Puncturing Through a Tissue Structure and Ablating a Tissue Region", the entire disclosure of which are incorporated herein by reference in its entirety.

In some embodiments, the catheter electrodes 17 can be constructed in the form of metallic bands or rings. In some embodiments, each electrode 17 can be constructed so as to be flexible. For example, the electrodes 17 can be in the form of metallic coiled springs or helical windings around the shaft of the catheter 15. As another example, the electrode(s) 17 can be in the form of a series of metallic bands or rings disposed along the shaft and that are electrically connected together, with the flexible portions of catheter shaft between the electrodes providing flexibility to the entire electrode. In some embodiments, at least a portion of the electrodes 17 can include biocompatible metals such as, but not limited to, titanium, palladium, silver, platinum and/or platinum alloys. In some embodiments, at least a portion of the electrodes 17 includes platinum and/or platinum alloys. In some embodiments, the catheter shaft can be made of a flexible polymeric material such as (for purposes of non-limiting examples only) polytetrafluorethylene, polyamides such as nylon, or polyether block amide. The electrodes 17 can be connected to insulated electrical leads (not shown) leading to a proximal handle portion of the catheter 15 (not shown), with the insulation on each of the leads being capable of sustaining an electrical potential difference of at least 700V across its thickness without dielectric breakdown. While the catheter 15 is placed epicardially as shown in FIG. 1, i.e. beneath the pericardium, in alternate embodiments the ablation catheter can be additionally or alternatively useful for endocardial placement.

It should be appreciated that the specific ablation devices and other examples provided herein are described for illustrative purposes, and a variety of other ablation devices configured for use in various tissue types and anatomies can benefit from the use of the waveforms described in the disclosure herein, without departing from the scope of the present invention.

Electrode Sequencing

Described herein are systems, devices, and methods for delivery of electroporation energy using a sequenced set of electrode pairings incorporating time delays and interleaving across a plurality of sets of electrode pairings during one or more heartbeats. In some embodiments, each electrode pairing may comprise a set of anodes paired with a set of cathodes. As described in more detail herein, during the group delay following a group of pulses associated with a first set of paired electrodes, a group of pulses associated with at least a second set of paired electrodes may be delivered so as to interleave the groups of pulses being delivered. This sequential delivery of pulses may occur over a plurality of sets of electrode pairings during each heartbeat for a predetermined number of successive or distinct heartbeats. In particular, for each electrode pairing, a plurality of groups of pulses may be delivered with a group delay between successive groups of pulses.

Ablation energy may be delivered over a predetermined number of heartbeats using any of the ablation systems and devices as described herein. In some embodiments, a set of m electrode pairings may be selected to deliver a set of pulses in a predetermined electrode pairing sequence. The m electrode pairings may be divided into n cliques. At least one of the n cliques may include a set of two or more anode-cathode electrode pairings.

At a minimum, a clique corresponds to an anode-cathode pairing of electrode subsets. However, a clique generally refers to a set of multiple electrode pairings (each pairing involving anode-cathode electrode subsets). For example, a first electrode pairing of anode $a_1$ with cathodes $c_1$ and $c_2$ may be represented by the notation ($a_1$-($c_1$,$c_2$)), and this defines a pairing of electrode subsets. Such a single pairing of electrode subsets may by itself define a clique. More generally, a clique may comprise multiple such pairings of electrode subsets. One useful embodiment or construction of cliques comprises two pairings of electrode subsets. Given m pairings of electrode subsets in a sequence of such pairings, if m is even, then these m pairings may be divided into m/2 cliques each comprising 2 pairings of electrode subsets. If m is odd, then one of the cliques will comprise a single pairing of electrode subsets and the other cliques will comprise 2 pairings of electrode subsets.

In another example, an electrode pairing sequence for a first heartbeat may include the following three electrode pairings: ($a_1$-($c_1$,$c_2$)), ($a_2$-($c_2$,$c_3$)), and ($a_3$-($c_3$,$c_4$)) where a first clique includes the first and second electrode pairs ($a_1$-($c_1$,$c_2$)) and ($a_2$-($c_2$,$c_3$)), and a second clique includes the third electrode pairing ($a_3$-($c_3$,$c_4$)).

The set of electrode pairings may deliver a plurality of groups of pulses having group time delays between successive groups of pulses. In some applications, group time delays may be relatively long (for example, several hundred or thousand microseconds), and this delay may be significantly longer than the duration of a single group of pulses.

However, during a group time delay period for a first electrode pairing, a group of pulses may be delivered using a second electrode pairing such that the groups of pulses from different electrode pairings are interleaved.

Figure 15:
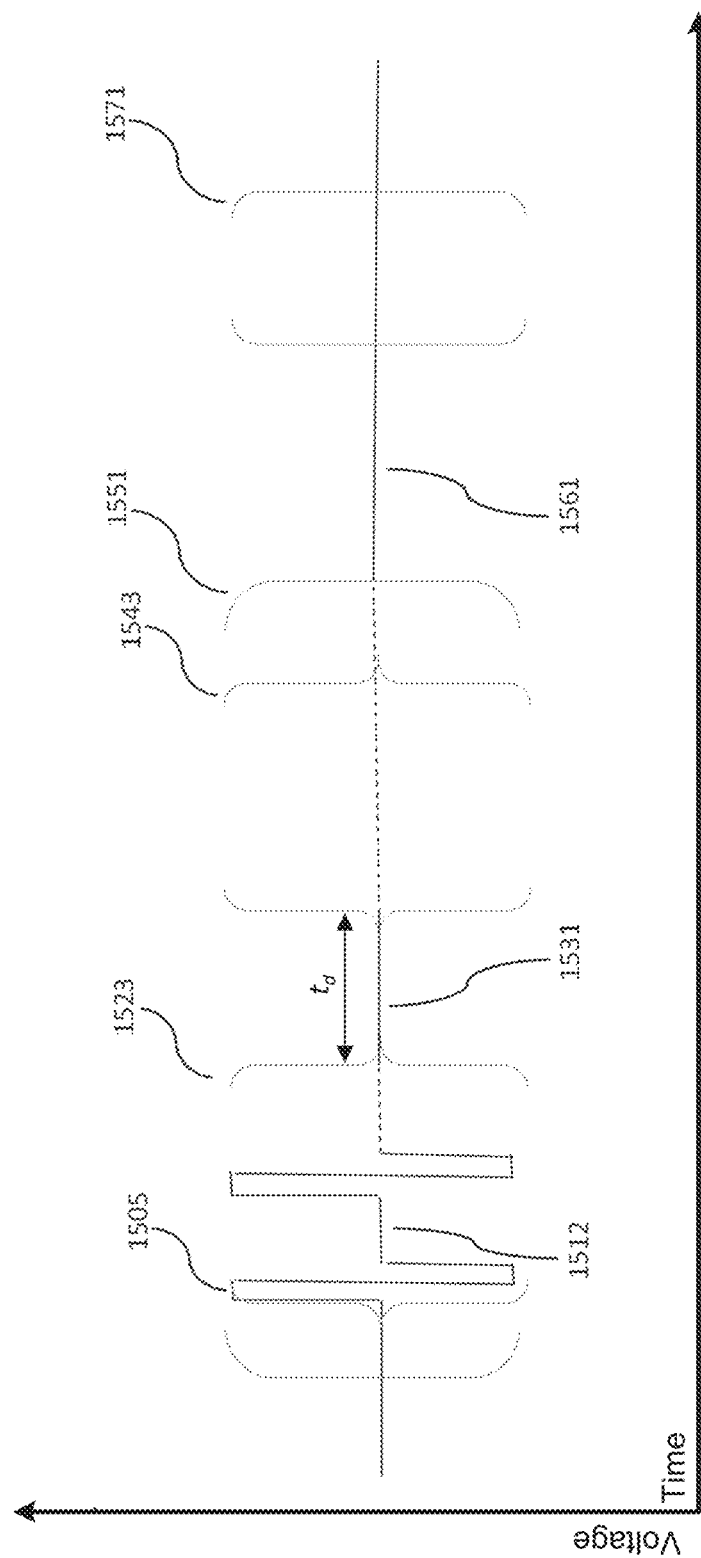
FIG. 15 schematically illustrates a hierarchy of pulses showing pulse widths, intervals between pulses, and groupings of pulses for an electrode pair, according to embodiments.

FIG. 15 illustrates p groups of pulses comprising a packet 1551 for a single electrode pairing with each group of pulses 1523, 1543 separated by a group time delay 1531 (of length $t_d$). A set of biphasic pulses 1505 may form a first group of pulses 1523. A second group of pulses 1543 is also illustrated with p such groups of pulses in the packet 1551 corresponding to a given electrode pairing during one heartbeat. Although this example illustrates biphasic pulses, monophasic pulses may also be used in some embodiments. A first level time interval 1512 may separate consecutive biphasic pulses 1505. Successive groups of pulses 1523 may be separated by a second level time interval 1531 (e.g., group time delay). In some embodiments, the length of the second level time interval 1531 may be at least three times the length of the first level time interval 1512. A number of packets of pulses 1551, 1571 may form a third level structure or a third level set of pulses (i.e., a super-packet). Successive packets of pulses 1551, 1571 may be separated by a third level time interval 1561. In some embodiments, the length of the third level time interval 1561 may be at least thirty times the length of the second level time interval 1531.

Figure 16:
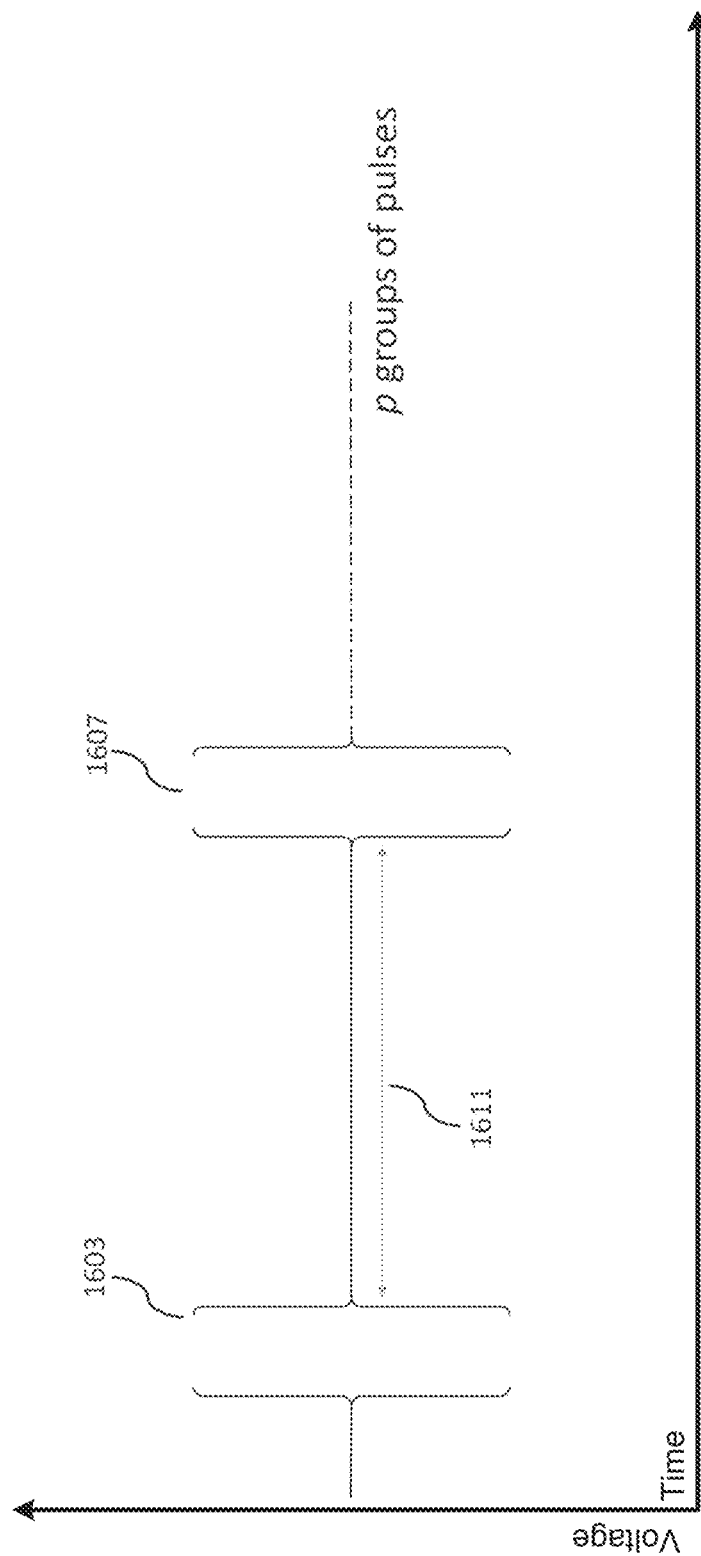
FIG. 16 schematically illustrates groups of pulses and a time delay between the groups of pulses for an electrode pair, according to embodiments.
Figure 17:
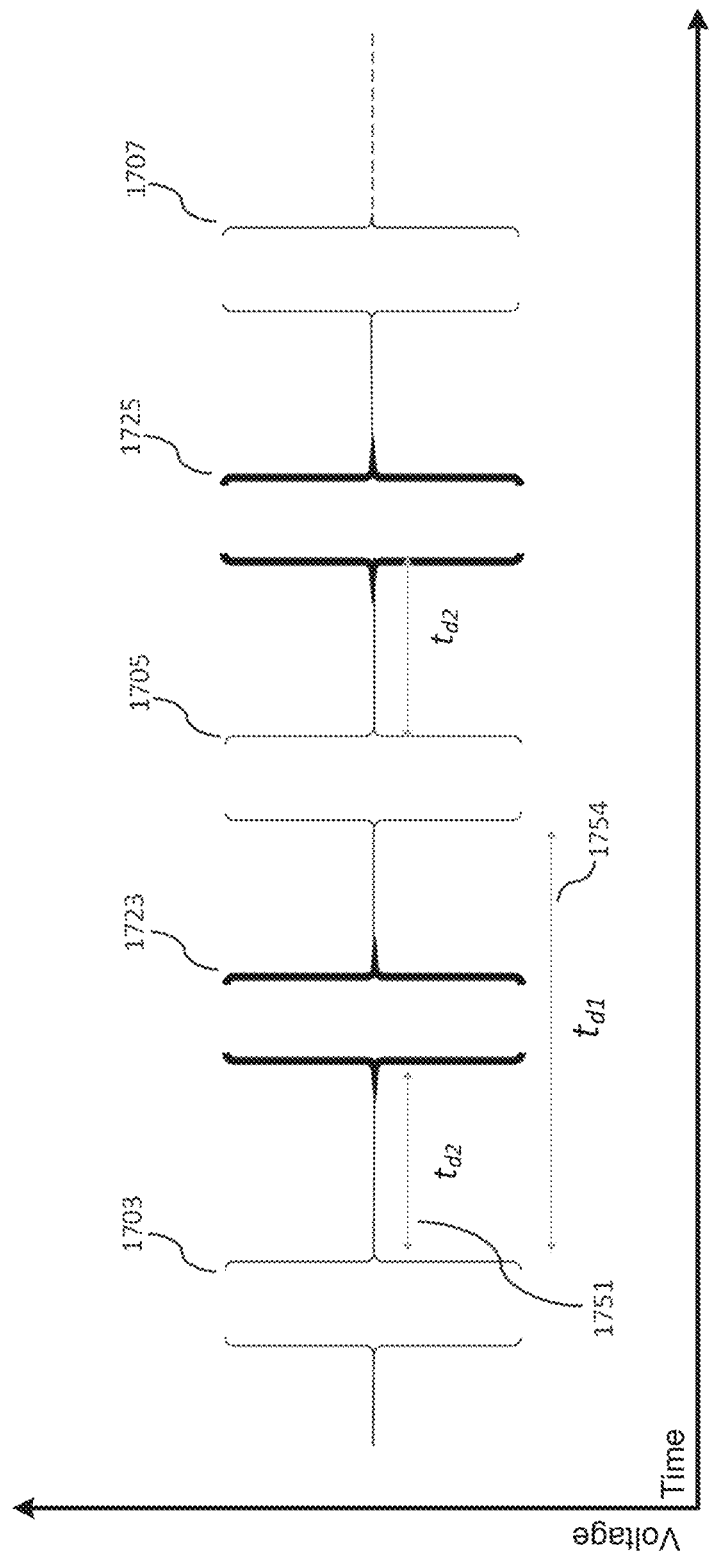
FIG. 17 schematically illustrates interleaved groups of pulses from two electrode sets of a two-element clique of electrode sets, according to embodiments.

FIG. 16 illustrates a set of a group of pulses 1603, 1607 and a time delay 1611 between the groups of pulses. In particular, a first group of pulses 1603 and a second group of pulses 1607 are separated by a group time delay interval 1611 having a duration or length $t_d$. In the interleaved (e.g., multiplexed) sequencing scheme disclosed herein, groups of pulses from a second electrode pairing set may be interleaved with groups of pulses from a first electrode pairing set in every clique of the electrode pairing sets. For example, after a time interval of $t_{d2}$ following a group of pulses corresponding to a first electrode pairing set, a group of pulses corresponding to a second electrode pairing set may be delivered. FIG. 17 illustrates interleaved groups of pulses from two electrode sets of a two-element clique of electrode pairing sets. In this manner, the complete delivery of energy over the desired electrode sequence may be efficiently performed. If instead of the interleaving illustrated in FIG. 17, the p groups of pulses for each electrode pairing are delivered sequentially over the set of electrode pairings, the delivery of ablation energy would take twice as long. A first electrode pairing set of a first clique may deliver a set of groups of pulses 1703, 1705, 1707 denoted by thin brackets in FIG. 17. Similarly, a second electrode pairing set of a first clique may deliver a set of groups of pulses 1723, 1725 denoted by thick brackets in FIG. 17. The groups of pulses of the first electrode pairing set may be separated by a time interval 1754 having a duration or length $t_{d1}$. A group of pulses 1703 of the first electrode pairing set may be followed by a group of pulses 1723 of the second electrode pairing set. For example, the group of pulses 1723 of the second electrode set is delivered at a time interval 1751 having a duration or length $t_{d2}$ following the group of pulses 1703 of the first electrode pairing set. In some embodiments, the duration $t_{d2}$ can be about half of $t_{d1}$ (e.g., less than about fifty-five percent of $t_{d1}$). It should be appreciated that in some embodiments, the time interval 1751 between groups of pulses of different electrode pairing sets may be other fractions of time relative to the time interval 1754 (i.e., fractions other than about half of $t_{d1}$, such as, for example, less than a third or a fourth of $t_{d1}$) corresponding to the group time delay for a given electrode pairing set.

Pulse delivery may be provided in a similar manner for every clique of a set of electrode pairings with interleaved groups of pulses for the two electrode sets in every clique (and no interleaving if the last clique comprises just one electrode set). A time delay interval (e.g., with duration $t_{d2}$) may be provided between successive groups of pulses corresponding to successive cliques of electrode pairing sets.

In some embodiments, the pulse delivery sequence shown in FIG. 17 may be applied using the electrode pairings ($a_1$-($c_1$,$c_2$)), ($a_2$-($c_2$,$c_3$)), and ($a_3$-($c_3$,$c_4$)) described herein where a first clique includes a first electrode pairing ($a_1$-($c_1$, $c_2$)) and a second electrode pairing ($a_2$-($c_2$,$c_3$)). A second clique may include a third electrode pairing ($a_3$-($c_3$,$c_4$)). For the first clique of electrode pairing sets, the p groups of pulses 1703, 1705, 1707, etc. of the first electrode pairing ($a_1$-($c_1$,$c_2$)) may be interleaved with the p groups of pulses 1723, 1725, etc. of the second electrode pairing ($a_2$-($c_2$,$c_3$)). After a time delay of length $t_{d2}$, the p groups of pulses for the third electrode pairing ($a_3$-($c_3$,$c_4$)) of the second clique may be delivered without interleaving.

Figure 18:
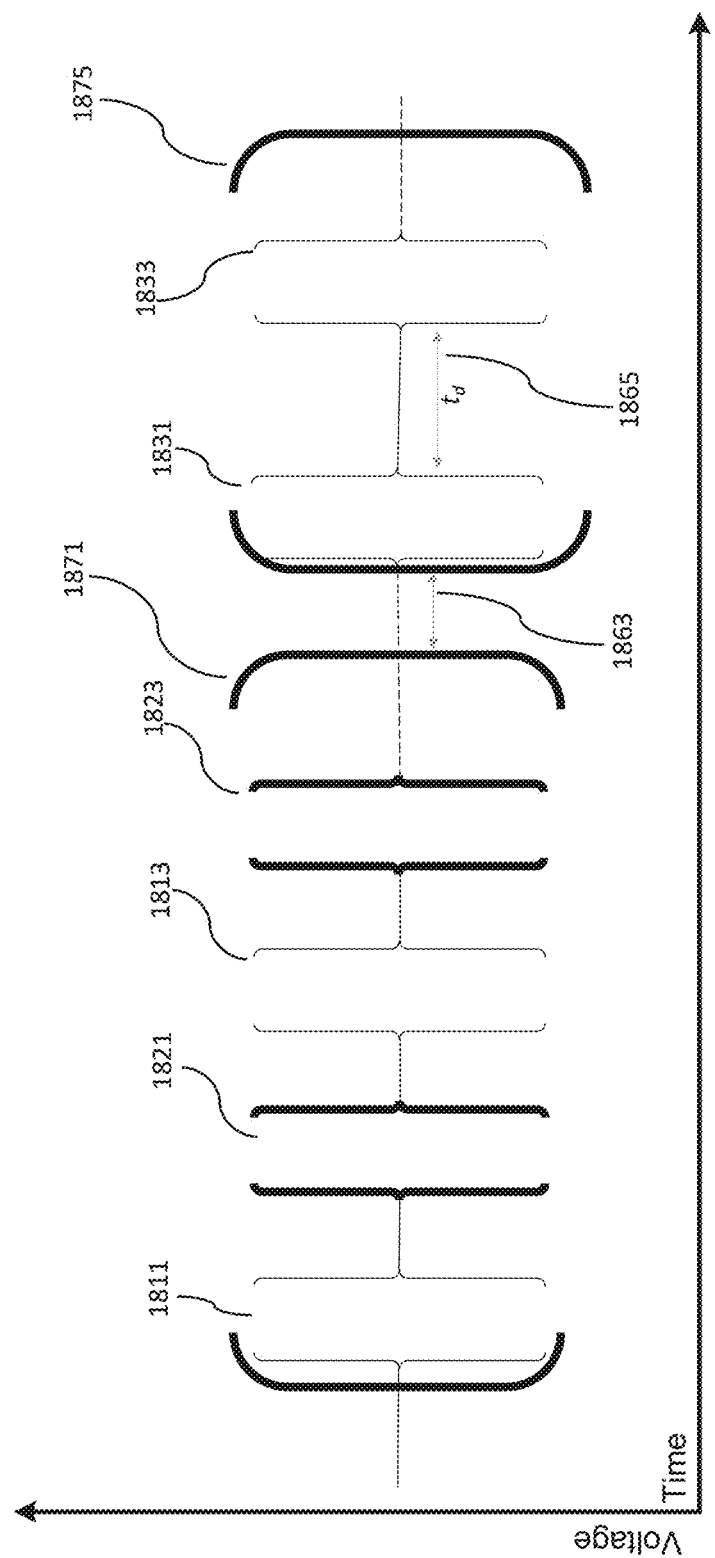
FIG. 18 schematically illustrates an ablation energy delivery sequence delivered over a heartbeat, according to embodiments.

FIG. 18 schematically illustrates an ablation delivery sequence delivered over a single heartbeat, according to embodiments. A first super group (or packet) of pulses 1871 of a first clique (($a_1$-($c_1$,$c_2$)) and ($a_2$-($c_2$,$c_3$))) are followed by a second super group of pulses 1875 of a second clique ($a_3$-($c_3$,$c_4$)). The first super group of pulses 1871 may include a set of groups of pulses 1811, 1813, etc. of a first electrode pairing ($a_1$-($c_1$,$c_2$)) and another set of groups of pulses 1821, 1823, etc. of a second electrode pairing ($a_2$-($c_2$,$c_3$)) that interleave (e.g., alternate, multiplex) over the p groups of pulses corresponding to each electrode set. A time delay 1863 may separate the pulse delivery of pulses 1871 of the first clique ($a_1$-($c_1$,$c_2$)) from the pulse delivery of pulses 1875 of the second clique ($a_2$-($c_2$,$c_3$)). The second super group of pulses 1875 may include a set of groups of pulses 1831, 1833 of just a third electrode pairing ($a_3$-($c_3$, $c_4$)) of a second clique. The groups of pulses 1831, 1833 may include p groups that may be each separated by a time interval 1865 having a duration or length $t_d$ corresponding to the group delay. In some embodiments, a group delay (such as the group delay in the examples herein) may be between about 10 µs and about 50 ms. While FIG. 18 illustrates sequenced ablation delivery for one heartbeat, similar sequences may be delivered for a predetermined number of heartbeats.

It should be noted that any number of electrode pairing sets may be defined and used as convenient for the implementation at hand; the above examples are provided for the sake of clarity and for exemplary purposes only. In some embodiments, the methods, systems, and devices disclosed herein may comprise one or more of the methods, systems, and devices described in one or more of International Application Serial No. PCT/US2018/029552, filed on Apr. 26, 2018, the contents of which are hereby incorporated by reference in its entirety.

Likewise, although the specific examples provided above illustrate pairwise sequencing where two-element cliques are defined, more generally n-element cliques of electrode sets may be defined, with interleaved sequences defined over the n-elements of each clique in a manner similar to that described in the specific example provided herein.

The interleaving or multiplexing processes described herein may increases the efficiency or speed with which an ablation energy sequence may be delivered in each heartbeat. This may be useful when there is a time constraint on delivering the entire ablation sequence over a heartbeat and/or within a refractory window of the cardiac chambers. In some embodiments, the ablation sequence of the electrode pairing sets may be defined independently for each heartbeat. In this case, the specific cliques defined in every heartbeat may be different. However, interleaving of the sequence may occur in a manner similar to that described herein.

While the interleaving or multiplexing of pulsed waveforms is described with reference to groups of pulses (e.g., first sets of pulses), as depicted in FIGS. 17 and 18, it can be appreciated that higher levels of hierarchy of a pulsed waveform can be interleaved between sets of electrodes. For example, voltage pulses delivered to a first electrode set and a second electrode set can be interleaved at higher levels of hierarchy, e.g., including a third level of hierarchy (e.g., interleaving of second sets of pulses), a fourth level of hierarchy (e.g., interleaving of third sets of pulses), and so on and so forth.

Additionally, in some embodiments, the specific sequence of interleaved electrode sets can vary over a number of heartbeats that in its entirety corresponds to the delivery of a series of second set of pulses (e.g., a third set of pulses) to each set of electrode pairings. For example, a sequence of interleaved electrode sets ($a_1$-$c_1$, $a_2$-$c_2$), ($a_3$-$c_3$, $a_4$-$c_4$) (with interleaving between the electrode sets inside each parenthesis) may be delivered during a first heartbeat, while the sequence of interleaved electrode sets ($a_3$-$c_3$, $a_4$-$c_4$), ($a_1$-$c_1$, $a_2$-$c_2$) may be delivered in the second heartbeat.

Furthermore, in some embodiments, one or more electrode sets may not appear in the ablation sequence during every heartbeat. For example, the interleaved electrode sets ($a_1$-$c_1$, $a_2$-$c_2$) may appear in the ablation sequence in the first heartbeat and in the third heartbeat, but not in the second heartbeat. In general, successive second sets of pulses for a given electrode set are delivered during distinct heartbeats, but not necessarily over successive heartbeats.

Hierarchical Waveforms

Figure 2:
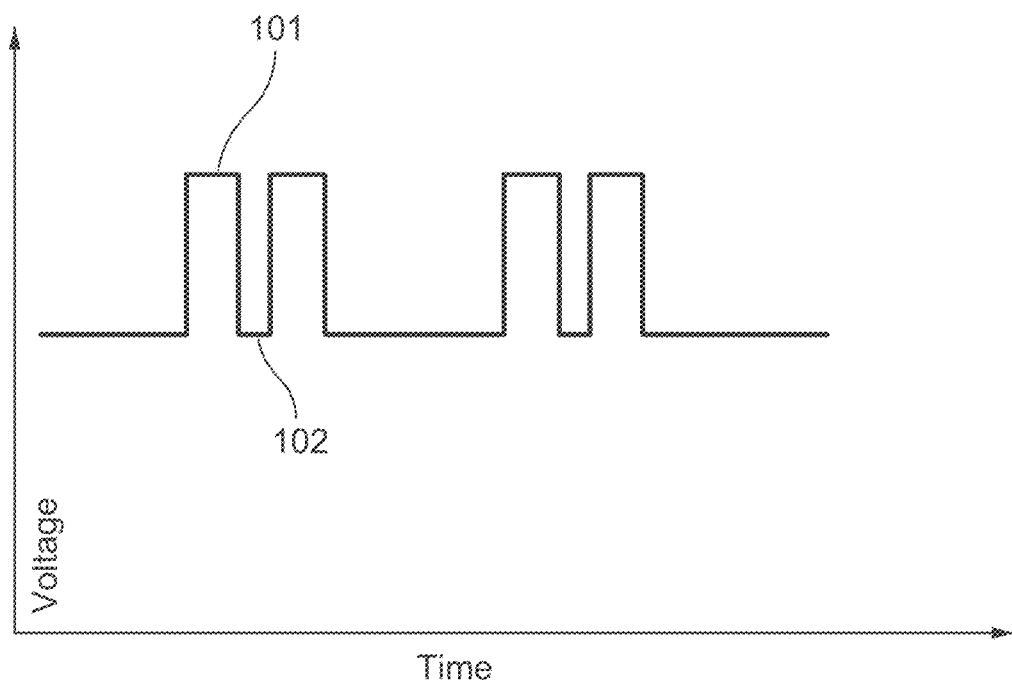
FIG. 2 is an example waveform showing a sequence of voltage pulses with a pulse width defined for each pulse, according to embodiments.

FIG. 2 illustrates a pulsed voltage waveform in the form of a sequence of rectangular double pulses, with each pulse, such as the pulse 101 being associated with a pulse width or duration. The pulse width/duration can be about 0.5 microseconds, about 1 microsecond, about 5 microseconds, about 10 microseconds, about 25 microseconds, about 50 microseconds, about 100 microseconds, about 125 microseconds, about 140 microseconds, about 150 microseconds, including all values and sub-ranges in between. The pulsed waveform of FIG. 2 illustrates a set of monophasic pulses where the polarities of all the pulses are the same (all positive in FIG. 2, as measured from a zero baseline). In some embodiments, such as for irreversible electroporation applications, the height of each pulse 101 or the voltage amplitude of the pulse 101 can be about 400 Volts, about 1000 Volts, about 5000 Volts, about 10,000 Volts, about 15,000 Volts, including all values and sub ranges in between. As illustrated in FIG. 2, the pulse 101 is separated from a neighboring pulse by a time interval 102, also sometimes referred to as a first time interval. The first time interval can be about 1 microsecond, 10 microseconds, about 50 microsecond, about 100 microseconds, about 200 microseconds, about 500 microseconds, about 800 microseconds, about 1 millisecond including all values and sub ranges in between, in order to generate irreversible electroporation.

Figure 3:
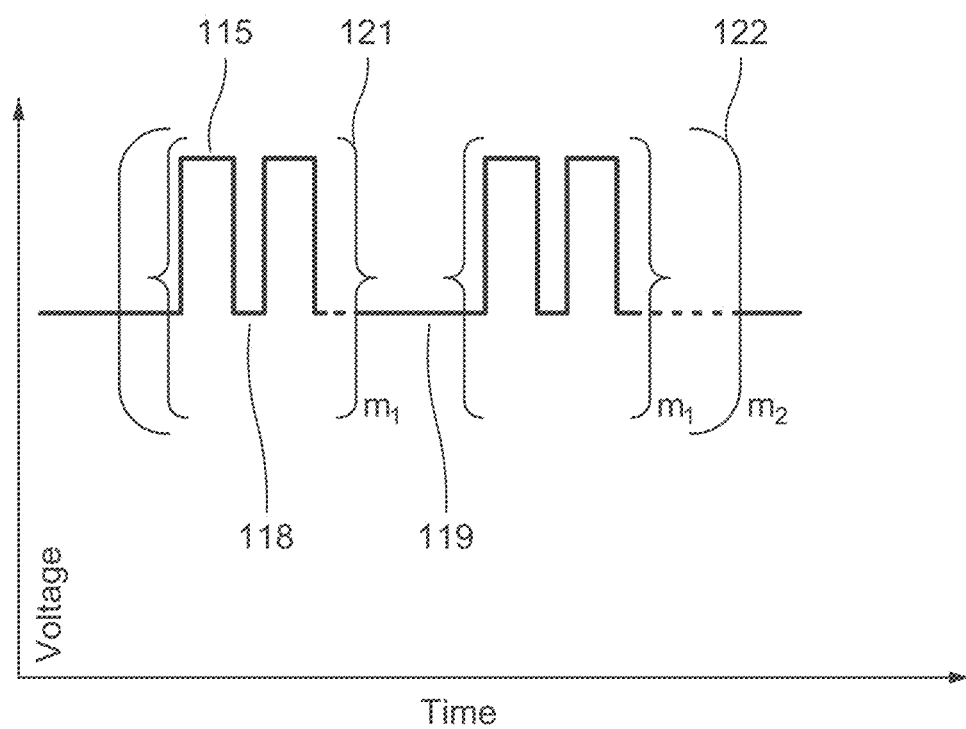
FIG. 3 schematically illustrates a hierarchy of pulses showing pulse widths, intervals between pulses, and groupings of pulses, according to embodiments.

FIG. 3 introduces a pulse waveform with the structure of a hierarchy of nested pulses. FIG. 3 shows a series of monophasic pulses such as pulse 115 with pulse width/pulse time duration w, separated by a time interval (also sometimes referred to as a first time interval or time delay) such as 118 of duration $t_1$ between successive pulses, a number $m_1$ of which are arranged to form a group of pulses 121 (also sometimes referred to as a first set of pulses). Furthermore, the waveform has a number $m_2$ of such groups of pulses (also sometimes referred to as a second set of pulses) separated by a time interval 119 (also sometimes referred to as a second time interval or time delay) of duration $t_2$ between successive groups. The collection of $m_2$ such pulse groups, marked by 122 in FIG. 3, constitutes the next level of the hierarchy, which can be referred to as a packet and/or as a second set of pulses. The pulse width w and the duration $t_1$ of time interval 118 between pulses can both be in the range of microseconds to hundreds of microseconds, including all values and sub ranges in between. In some embodiments, the duration $t_2$ of time interval 119 can be at least three times larger than the duration $t_1$ of time interval 118. In some embodiments, the ratio $t_2/t_1$ can be in the range between about 3 and about 300, including all values and sub-ranges in between.

Figure 4:
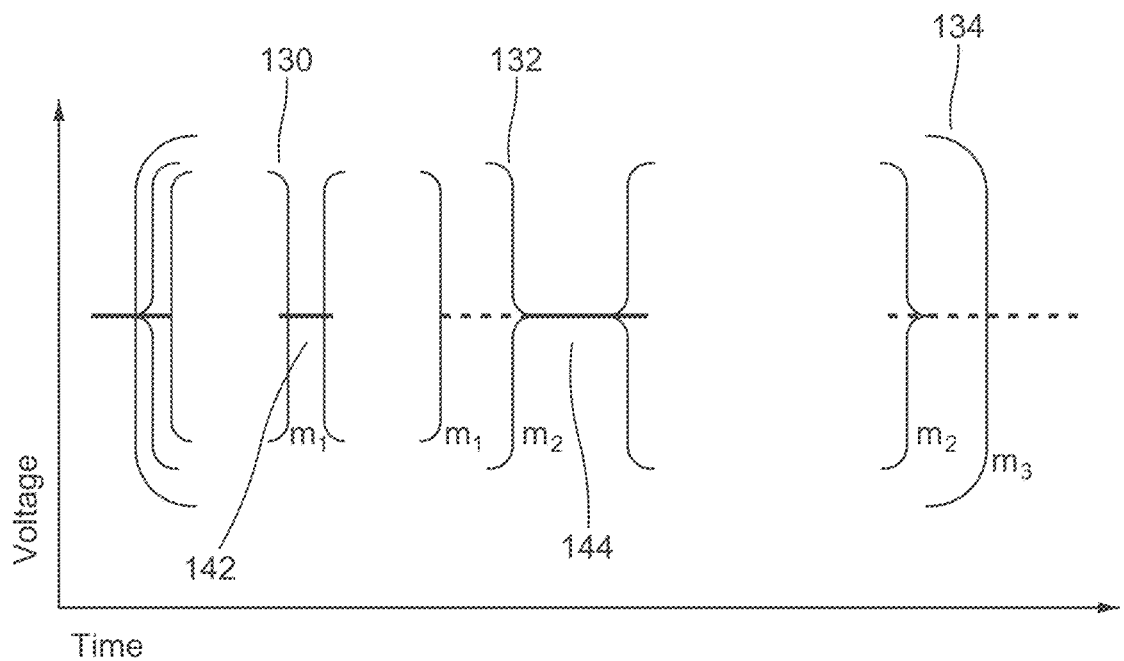
FIG. 4 provides a schematic illustration of a nested hierarchy of monophasic pulses displaying different levels of nested hierarchy, according to embodiments.

FIG. 4 further elaborates the structure of a nested pulse hierarchy waveform. In this figure, a series of $m_1$ pulses (individual pulses not shown) form a group of pulses 130 (e.g., a first set of pulses). A series of $m_2$ such groups separated by an inter-group time interval 142 of duration $t_2$ (e.g., a second time interval or time delay) between one group and the next form a packet 132 (e.g., a second set of pulses). A series of $m_3$ such packets separated by time intervals 144 of duration $t_3$ (e.g., a third time interval) between one packet and the next form the next level in the hierarchy, a super-packet labeled 134 (e.g., a third set of pulses) in the figure. In some embodiments, the time interval $t_3$ can be at least about thirty times larger than the time interval $t_2$. In some embodiments, the time interval $t_3$ can be at least fifty times larger than the time interval $t_2$. In some embodiments, the ratio $t_3/t_2$ can be in the range between about 30 and about 800, including all values and sub-ranges in between. The amplitude of the individual voltage pulses in the pulse hierarchy can be anywhere in the range from 500 Volts to 7,000 Volts or higher, including all values and sub ranges in between. The individual pulses in the first set of pulses may be either monophasic pulses or biphasic pulses, or may comprise a combination of monophasic and biphasic pulses.

Figure 14:
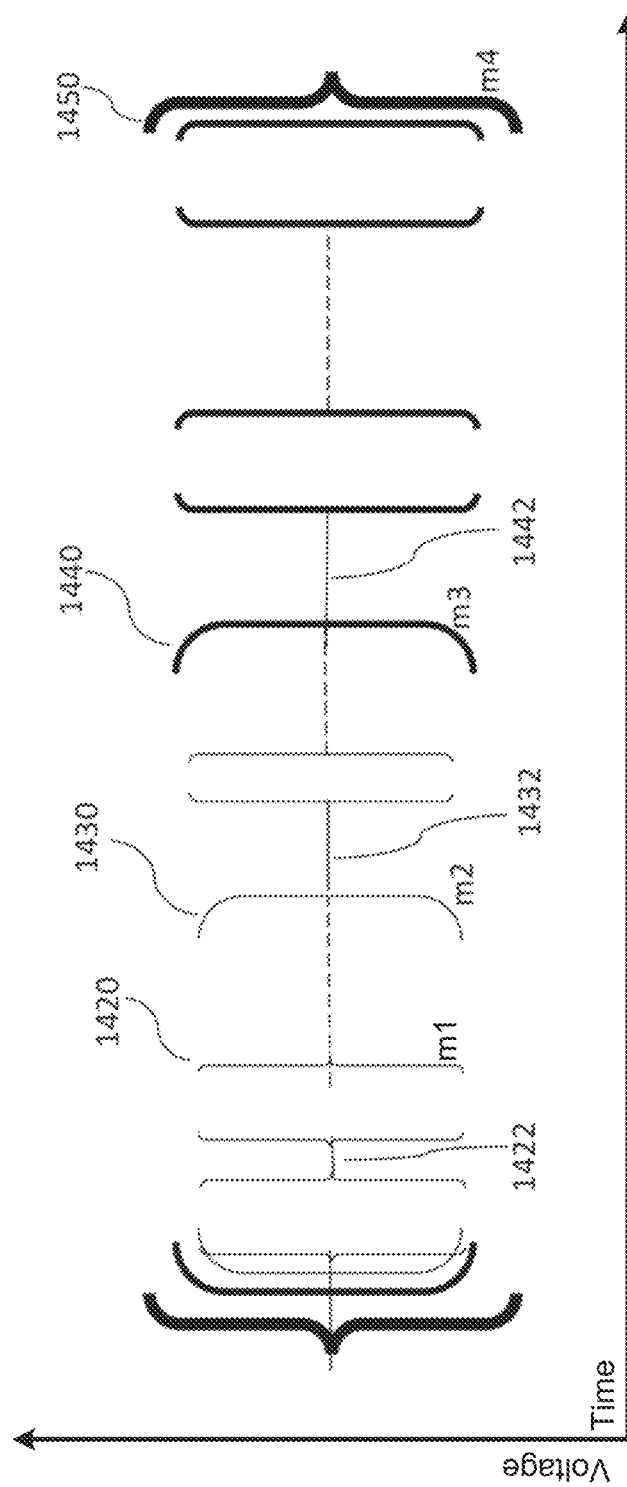
FIG. 14 schematically illustrates a hierarchy of pulses showing pulse widths, intervals between pulses, and groupings of pulses, according to embodiments.

FIG. 14 even further elaborates the structure of a nested pulse hierarchy waveform. In this figure, a series of $m_1$ pulses (individual pulses not shown) form a group of pulses 1420 (e.g., a first set of pulses). A series of $m_2$ such groups separated by an inter-group time interval 1422 of duration $t_2$ (e.g., a second time interval or time delay) between one group and the next form a packet 1430 (e.g., a second set of pulses). A series of $m_3$ such packets separated by time intervals 1432 of duration $t_3$ (e.g., a third time interval or time delay) between one packet and the next form the next level in the hierarchy, a super-packet labeled 1440 (e.g., a third set of pulses) in the figure. In some embodiments, the duration $t_3$ of time interval 1432 can be at least about thirty times larger than the duration $t_2$ of time interval 1422. In some embodiments, the duration $t_3$ of time interval 1432 can be in the range of about hundreds of milliseconds or tenths of a second. Further, there can be a series or multiplicity of $m_4$ super-packets such as 1440 separated by a time interval 1442 of duration $t_4$ that comprise a further level of the hierarchy (e.g., a fourth set of pulses), referred to as a super-super-packet. In some embodiments, the number $m_4$ of super-packets can be any integer ranging between 1 to 50, including all values and sub-ranges in between. In some embodiments, the duration $t_4$ of time interval 1442 can be at least ten times larger than the duration $t_3$ of time interval 1432. In some embodiments, the duration $t_4$ of the time interval 1442 can be in the range of about seconds to about minutes. In some embodiments, the ratio $t_4/t_3$ can be in the range between about 10 and about 1000, including all values and sub-ranges in between. In some embodiments, the duration $t_4$ of the time interval 1442 between individual super-packets can be constant across all the $m_4$ super-packets. Alternatively, the duration $t_4$ of the time interval 1442 can vary among different pairs of super-packets. One or more of the time intervals 1442 may have durations that are manually selected or randomly set above a minimum threshold duration. The minimum threshold duration may be in the range of several seconds (e.g., 5 seconds or more). In some embodiments, the time intervals 1442 can have durations that vary according to a sequence or pattern. For example, a group of super-packets within the $m_4$ super-packets can include pairs of super-packets that are successively separated by a sequence of time intervals with durations $t_{4,1}, t_{4,2}, t_{4,3}, \ldots t_{4,q}$ (with q being any integer greater than 1), the values for $t_{4,1}, t_{4,2}, t_{4,3}, \ldots t_{4,q}$ being selected within a suitable range of values (e.g., durations in the range of seconds, tens of seconds, or minutes). The sequence of time intervals $t_{4,1}, t_{4,2}, t_{4,3}, \ldots t_{4,q}$ can further be repeated across additional groups of super-packets for any number of times to further generate additional portions of a pulse waveform. The amplitude of the individual voltage pulses in the pulse hierarchy can be anywhere in the range from 500 Volts to 7,000 Volts or higher, including all values and sub ranges in between.

In some embodiments, when the pulse waveform is delivered in synchrony with cardiac cycles of the heart, individual super-packets (e.g., third sets of pulses) can extend across multiple cardiac cycles of the heart, with packets of pulses including one or more groups of pulses being delivered during each cardiac cycle (e.g., during a refractory period of the cardiac cycles). In some embodiments, each time interval or time delay between successive super-packets (e.g., a third time interval or third time delay) can approximately correspond to a duration of a cardiac cycle, such that successive super-packets can be delivered during successive cardiac cycles of the heart (e.g., during their refractory period). In some embodiments, each time interval or time delay separating successive super-super-packets (e.g., fourth time interval or time delay) can be greater than a cardiac cycle of the heart. In some embodiments, as described herein, systems and methods can include a cardiac stimulation device or cardiac stimulator that can generate pacing pulses to synchronize the delivery of the pulse waveform with the cardiac cycles of the heart.

The multiplicity of the third level of pulses comprising the fourth set of pulses may provide more effective treatment or therapy delivery. Nanopores in cell membranes that are reversibly opened by a single third set of pulses may be irreversibly opened by applying a multiplicity of third set of pulses, thereby generating a larger ablation zone. For example, in a clinical application, after delivering a first third set of pulses for ablation delivery, there can be a time interval or pause $t_4$ in the range of between about 5 seconds and about 500 seconds before a second third set of pulses is delivered to continue ablation delivery. This type of ablation delivery may be beneficial from a therapeutic perspective and may deliver a more complete treatment for certain cardiac arrhythmia conditions. For example, it may ensure generation of ablation zones that are contiguous and trans-mural across an atrial wall. In some embodiments, subsequent third sets of pulses may be delivered as well. In some embodiments, the time intervals between consecutive third sets of pulses may vary rather than being fixed. In some embodiments, a minimum value of the duration $t_4$ of time intervals between successive third sets of pulses may be set by the generator to support this delivery mode for higher levels of the hierarchy in the pulse waveform structure. In some embodiments, the minimum value of the duration $t_4$ of the time interval may be at least about 5 seconds.

Figure 19:
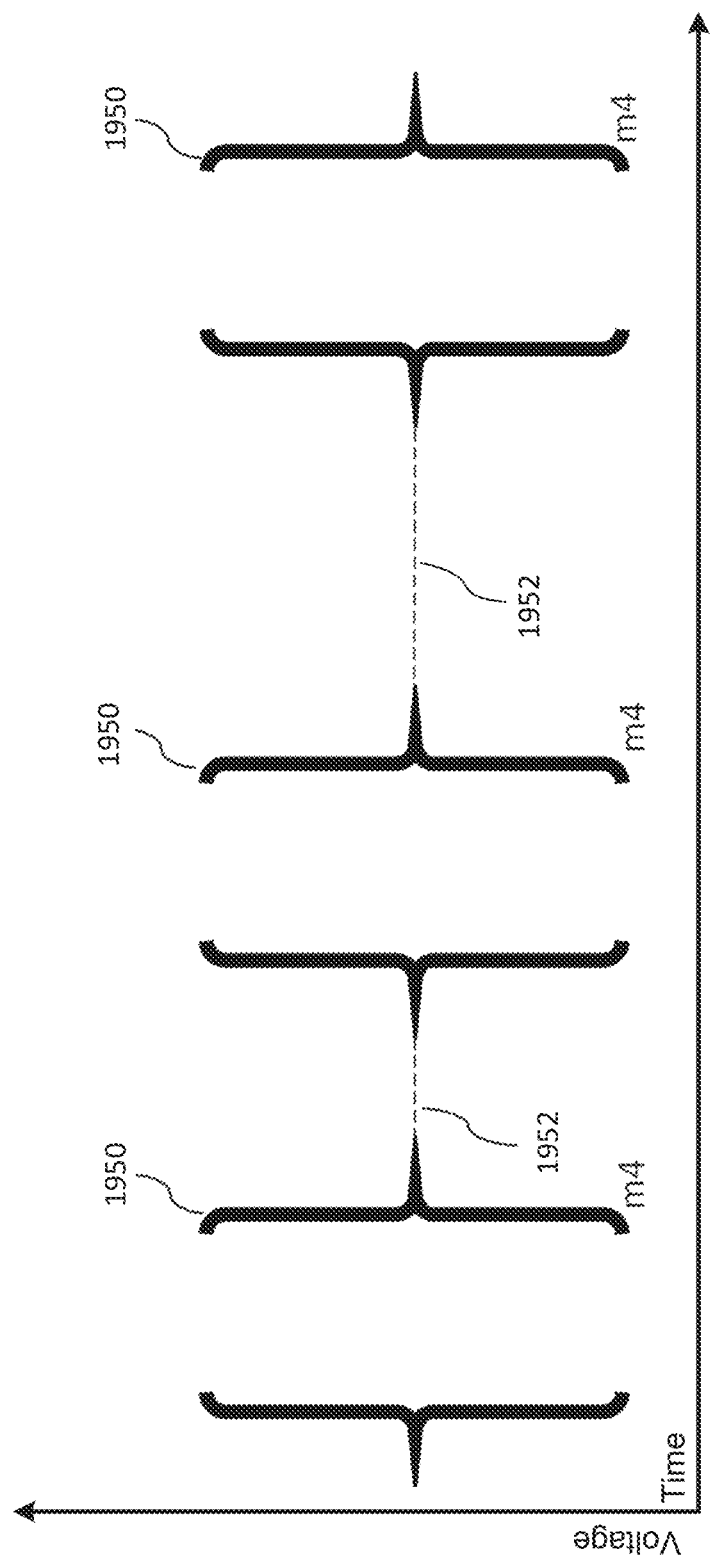
FIG. 19 schematically illustrates a hierarchy of pulses showing pulse widths, intervals between pulses, and groupings of pulses for an electrode pair, according to embodiments.

FIG. 19 further elaborates the structure of a pulsed hierarchy waveform, according to embodiments. The waveform illustrated in FIG. 19 adds another level of hierarchy over the waveform illustrated and described with reference to FIG. 14. In particular, the waveform in FIG. 19 can include the structure of the nested pulse hierarchy waveform according to FIG. 14, and include another level in the hierarchy of multiplicity of pulses.

As described with reference to FIG. 14, a fourth level of hierarchy of a nested pulse hierarchy waveform can include a series or multiplicity of $m_4$ super-packets that form a super-super-packet. Each super-packet can include a series or multiplicity of $m_3$ packets, each packet can include a series or multiplicity of $m_2$ groups, and each group can include a series or multiplicity of $m_1$ pulses.

The notion of a hierarchy can be further generalized in an iterative fashion, with reference to FIG. 19. As depicted in FIG. 19, a series of super-super-packets 1950 (each including a series of $m_4$ super-packets, not shown in FIG. 19) can be separated by time intervals 1952 of a duration $t_5$. The total duration of each of the super-super-packets 1950 and time intervals 1952 can vary or be the same across the series of super-super-packets 1950 and time intervals 1952. This series of super-super-packets 1950 can form a higher level of the pulse waveform hierarchy (e.g., a fifth set of pulses), which can be referred to as a hyper packet.

The multiplicity of the fourth level of pulses comprising the fifth set of pulses may, under some circumstances, provide more effective treatment or therapy delivery. While the waveform illustrated in FIG. 19 is described to include a fifth level of hierarchy with a fifth set of pulses, a successive generation of waveforms with any number of even higher levels of hierarchies including higher levels of pulses can be appreciated. For example, waveforms with a sixth level, seventh level, etc., can be generated to each include a sixth set of pulses, a seventh set of pulses, etc., respectively.

Each level of hierarchy of pulses can be defined by a multiplicity or series of the set of pulses from the next lower level of hierarchy, each set of pulses from the lower level of hierarchy being separated from the next by a time interval or time delay. The duration of the time interval separating successive sets of pulses from the lower level of hierarchy can be constant or vary across the series, as described above with reference to FIG. 14. For example, a $r^{th}$ level of hierarchy can include a series of sets of pulses from the r-1 level and time intervals $t_r$ separating each set of pulses from the r-1 level.

As described previously with reference to the waveform illustrated in FIG. 14, nanopores in cell membranes that are reversibly opened by a single $r^{th}$ set of pulses may be irreversibly opened by applying a multiplicity of $r^{th}$ set of pulses, thereby generating a larger ablation zone. For example, in some clinical applications, after delivering a first $r^{th}$ set of pulses for ablation delivery, there can be a time interval or pause in the range of between about 5 seconds and about 500 seconds before a second $r^{th}$ set of pulses is delivered to continue ablation delivery, when r is greater than 3. This type of ablation delivery may be beneficial from a therapeutic perspective and may deliver a more complete treatment for certain cardiac arrhythmia conditions. For example, it may ensure generation of ablation zones that are contiguous and transmural across an atrial wall. In some embodiments, subsequent $r^{th}$ sets of pulses may be delivered as well. In some embodiments, the time intervals between consecutive $r^{th}$ sets of pulses may vary rather than being fixed. In some instances, a therapeutic strategy may be developed to include ablation delivery via waveforms with varying levels of hierarchy, including varying time intervals, number of pulses and/or pulse intensities. For example, therapeutic strategies can include ablation delivered using waveforms with successively increasing or decreasing levels of hierarchy, successively increasing or decreasing number of pulses in each level of hierarchy, or successively increasing or decreasing time intervals between pulses in each level of hierarchy, to achieve a more complete treatment for certain cardiac arrhythmia conditions. In some embodiments, a minimum value of the time interval between successive $r^{th}$ sets of pulses may be set by the generator to support this delivery mode for higher levels of the hierarchy in the pulse waveform structure. In some embodiments, the minimum value of the time interval may be at least about 5 seconds, when r is greater than 3.

Figure 5:
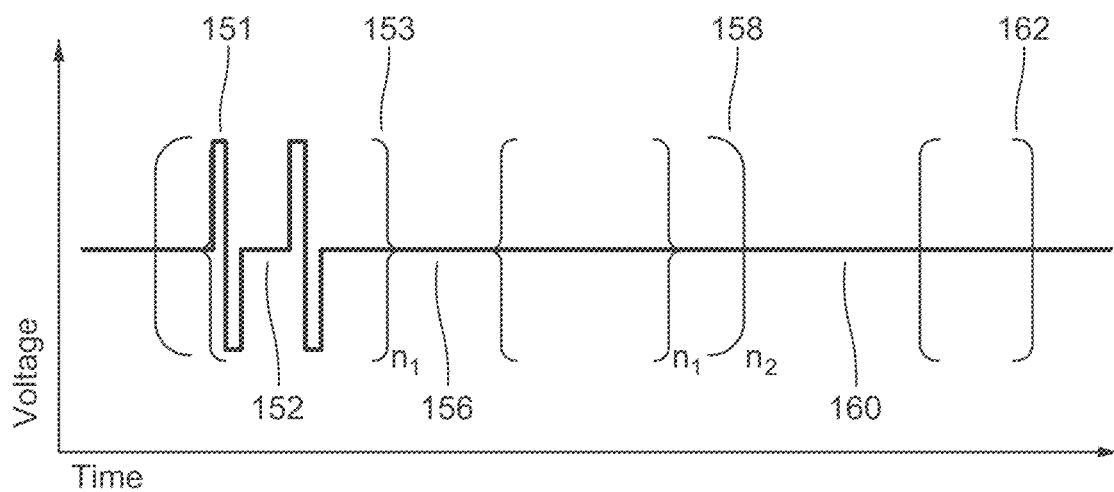
FIG. 5 is a schematic illustration of a nested hierarchy of biphasic pulses displaying different levels of nested hierarchy, according to embodiments.

FIG. 5 provides an example of a biphasic waveform sequence with a hierarchical structure. In the example shown in the figure, biphasic pulses such as 151 have a positive voltage portion as well as a negative voltage portion to complete one cycle of the pulse. There is a time delay 152 (e.g., a first time interval) between adjacent cycles of duration $t_1$, and $n_1$ such cycles form a group of pulses 153 (e.g., a first set of pulses). A series of $n_2$ such groups separated by an inter-group time interval 156 (e.g., a second time interval) of duration $t_2$ between one group and the next form a packet 158 (e.g., a second set of pulses). The figure also shows a second packet 162, with a time delay 160 (e.g., a third time interval) of duration $t_3$ between the packets. Just as for monophasic pulses, higher levels of the hierarchical structure can be formed as well. The amplitude of each pulse or the voltage amplitude of the biphasic pulse can be anywhere in the range from 500 Volts to 7,000 Volts or higher, including all values and sub ranges in between. The pulse width/pulse time duration can be in the range from nanoseconds or even sub-nanoseconds to tens of microseconds, while the delays $t_1$ can be in the range from zero to several microseconds. The inter-group time interval $t_2$ can be at least ten times larger than the pulse width. In some embodiments, the time interval $t_3$ can be at least about twenty times larger than the time interval $t_2$. In some embodiments, the time interval $t_3$ can be at least fifty times larger than the time interval $t_2$.

Embodiments disclosed herein include waveforms structured as hierarchical waveforms that include waveform elements/pulses at various levels of the hierarchy. The individual pulses such as 115 in FIG. 3 comprise the first level of the hierarchy, and have an associated pulse time duration and a first time interval between successive pulses. A set of pulses, or elements of the first level structure, form a second level of the hierarchy such as the group of pulses/second set of pulses 121 in FIG. 3. Among other parameters, associated with the waveform are parameters such as a total time duration of the second set of pulses (not shown), a total number of first level elements/first set of pulses, and second time intervals between successive first level elements that describe the second level structure/ second set of pulses. In some embodiments, the total time duration of the second set of pulses can be between about 20 microseconds and about 10 milliseconds, including all values and sub-ranges in between. A set of groups, second set of pulses, or elements of the second level structure, form a third level of the hierarchy such as the packet of groups/third set of pulses 122 in FIG. 3. Among other parameters, there is a total time duration of the third set of pulses (not shown), a total number of second level elements/second set of pulses, and third time intervals between successive second level elements that describe the third level structure/third set of pulses. In some embodiments, the total time duration of the third set of pulses can be between about 60 microseconds and about 250 milliseconds, including all values and sub ranges in between.

In some embodiments, a set of grouped third set of pulses may form a fourth level of the hierarchy such as a super-super-packet comprising a multiplicity of third set of pulses (e.g., third set of pulses 1430) that defines a fourth set of pulses (e.g., fourth set of pulses 1440), see FIG. 14. Further, as described with reference to FIG. 19, a multiplicity or series of fourth set of pulses (e.g. super-super-packets) may form a fifth level of the hierarchy, such as in the waveform illustrated in FIG. 19. While specific levels of hierarchy are described with reference to the figures, it can be appreciated that iterative generation of waveforms with any number of higher levels of hierarchies including higher levels of pulses can be used to perform an ablation procedure, depending on the factors and/or requirements of a particular procedure. Such higher level generalizations are described above, with reference to FIG. 19.

Among other parameters, there is a total time duration of the fourth set of pulses (not shown), a total number of fourth level elements/fourth set of pulses, and fourth time intervals between successive fourth level elements that describe a fifth level structure. In some embodiments, the total time duration of the fourth set of pulses may be between about 100 milliseconds and about 15 minutes, including all values and sub ranges in between. The time duration between successive fourth sets of pulses can range between about 5 seconds and between 500 seconds. The generally iterative or nested structure of the waveforms can continue to a higher plurality of levels, such as ten levels of structure, or more.

In some embodiments, hierarchical waveforms with a nested structure and hierarchy of time intervals as described herein are useful for irreversible electroporation ablation energy delivery, providing a good degree of control and selectivity for applications in different tissue types. A variety of hierarchical waveforms can be generated with a suitable pulse generator. It is understood that while the examples herein identify separate monophasic and biphasic waveforms for clarity, it should be noted that combination waveforms, where some portions of the waveform hierarchy are monophasic while other portions are biphasic, can also be generated/implemented.

In embodiments directed to treatment of cardiac ablation, the pulse waveforms described above can be applied with electrode bipoles selected from a set of electrodes on a catheter, such as an ablation catheter. A subset of electrodes of the catheter can be chosen as anodes, while another subset of electrodes of the ablation catheter can be chosen as cathodes, with the voltage waveform being applied between anodes and cathodes. As a non-limiting example, in instances where the ablation catheter is an epicardially placed ablation catheter, the catheter can be wrapped around the pulmonary veins, and one electrode can be chosen as anode and another electrode can be chosen as cathode. FIG.

Figure 6:
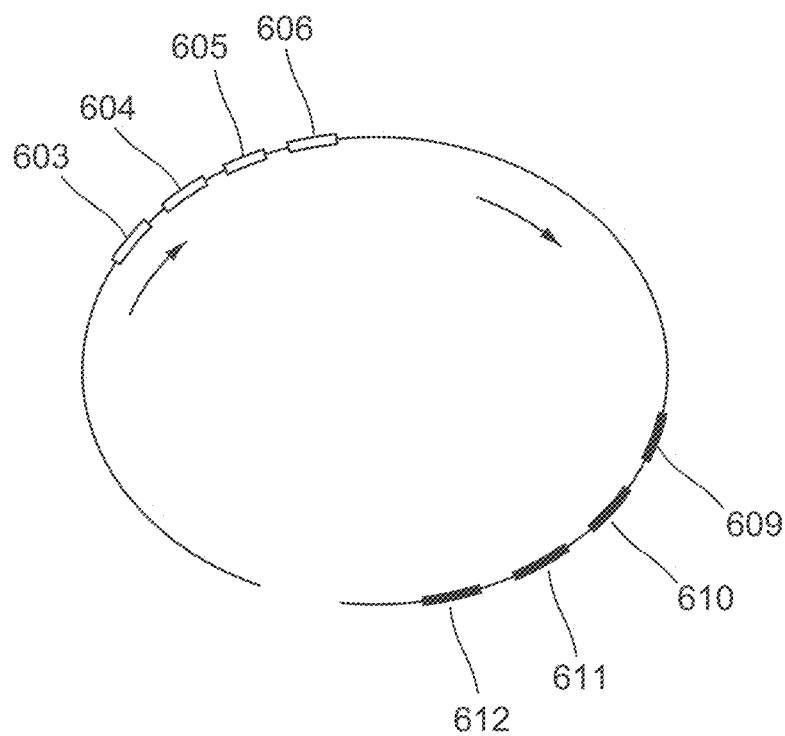
FIG. 6 schematically shows a circle of numbered catheter electrodes, wherein sets of electrodes can be sequentially selected for application of a corresponding sequence of voltage pulse waveforms, according to embodiments.

6 illustrates an example circular catheter configuration, where approximately diametrically opposite electrode pairs (e.g., electrodes 603 and 609, electrodes 604 and 610, electrodes 605 and 611, and electrodes 606 and 612) are activatable as anode-cathode sets. Any of the pulse waveforms disclosed can be progressively or sequentially applied over a sequence of such electrode sets. As a non-limiting example, FIG. 6 depicts a sequence of electrode subset activations. As a first step, electrodes 603 and 609 are selected as anode and cathode respectively, and a voltage waveform with a hierarchical structure (e.g., the waveform of FIG. 14) described herein is applied across these electrodes. With a small time delay (e.g., less than about 5 milliseconds), as a next step electrodes 604 and 610 are selected as anode and cathode respectively, and the waveform is applied again across this set of electrodes. After a small time delay, as a next step electrodes 605 and 611 are selected as anode and cathode respectively for the next application of the voltage waveform. In the next step, after a small time delay, electrodes 606 and 612 are selected as anode and cathode respectively for voltage waveform application. In some embodiments, one or more of the waveforms applied across electrode pairs is applied during the refractory period of a cardiac cycle, as described in more detail herein.

Figure 7:
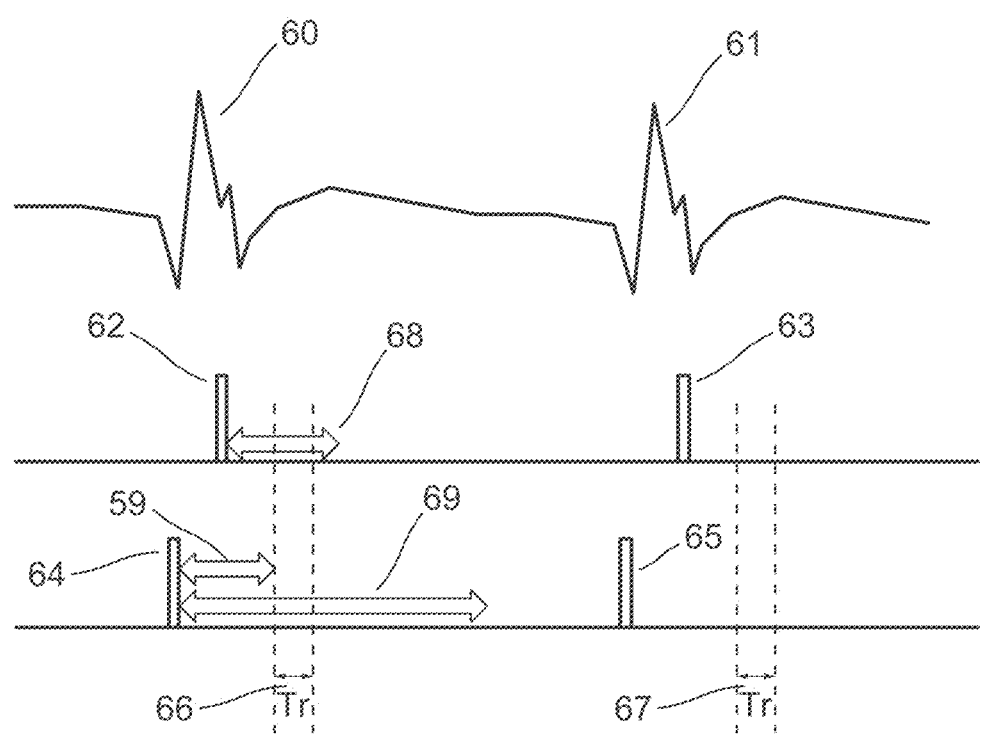
FIG. 7 illustrates schematically a time sequence of electrocardiograms and cardiac pacing signals together with atrial and ventricular refractory time periods and indicating a time window for irreversible electroporation ablation, according to embodiments.

In some embodiments, the ablation pulse waveforms described herein are applied during the refractory period of the cardiac cycle so as to avoid disruption of the sinus rhythm of the heart. In some embodiments, a method of treatment includes electrically pacing the heart with a cardiac stimulator to ensure pacing capture to establish periodicity and predictability of the cardiac cycle, and then defining a time window within the refractory period of the cardiac cycle within which one or more pulsed ablation waveforms can be delivered. FIG. 7 illustrates an example where both atrial and ventricular pacing is applied (for instance, with pacing leads or catheters situated in the right atrium and right ventricle respectively). With time represented on the horizontal axis, FIG. 7 illustrates a series of ventricular pacing signals such as 64 and 65, and a series of atrial pacing signals such as 62 and 63, along with a series of ECG waveforms 60 and 61 that are driven by the pacing signals. As indicated in FIG. 7 by the thick arrows, there is an atrial refractory time window 68 and a ventricular refractory time window 69 that respectively follow the atrial pacing signal 62 and the ventricular pacing signal 64. As shown in FIG. 7, a common refractory time window 66 of duration $T_r$ can be defined that lies within both atrial and ventricular refractory time windows 68, 69. In some embodiments, the electroporation ablation waveform(s) can be applied in this common refractory time window 66. The start of this refractory time window 68 is offset from the pacing signal 64 by a time offset 59 as indicated in FIG. 7. The time offset 59 can be smaller than about 25 milliseconds, in some embodiments. At the next heartbeat, a similarly defined common refractory time window 67 is the next time window available for application of the ablation waveform(s). In this manner, the ablation waveform(s) may be applied over a series of heartbeats, at each heartbeat remaining within the common refractory time window. In one embodiment, each packet of pulses as defined above in the pulse waveform hierarchy can be applied over a heartbeat, so that a series of packets is applied over a series of heartbeats, for a given electrode set.

Figure 8:
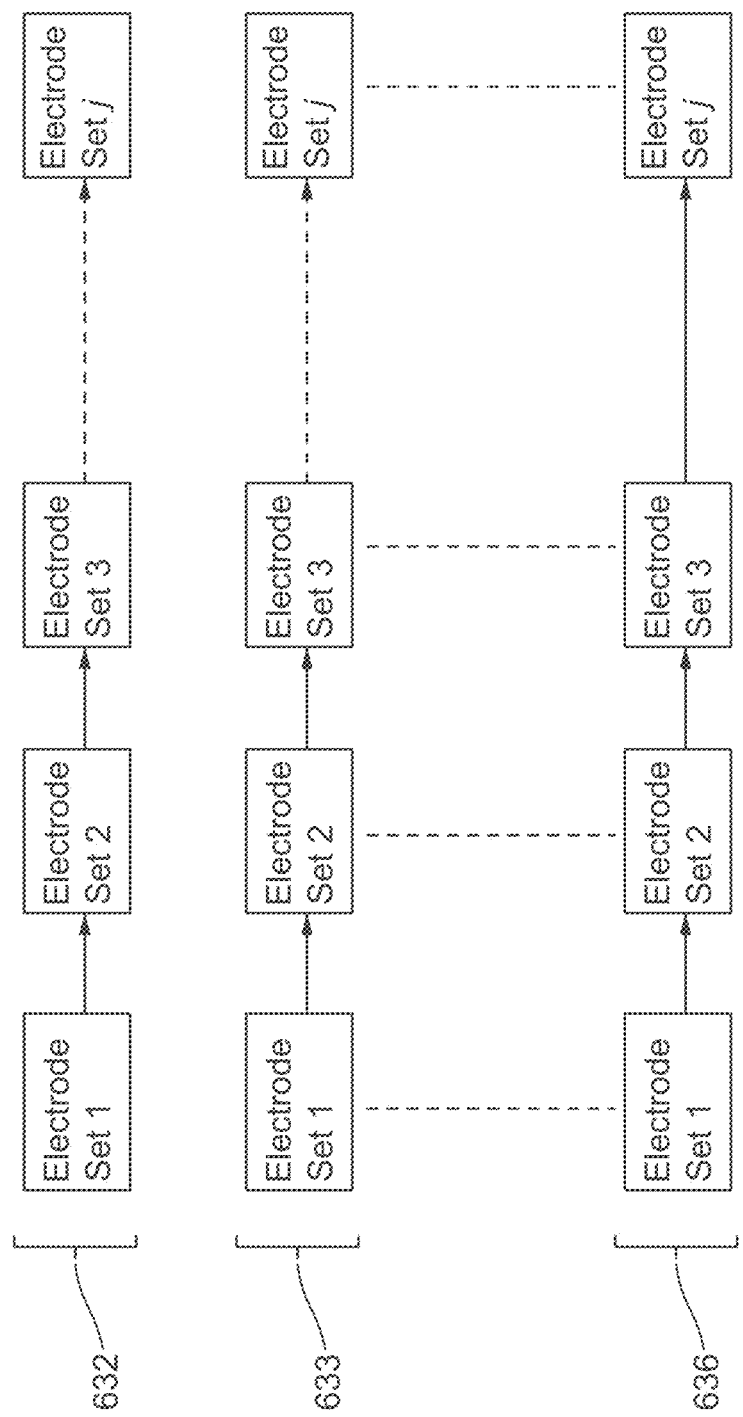
FIG. 8 illustrates schematically a time sequence of electrode set activations delivered as a series of waveform packets over a corresponding series of successive heartbeats, according to embodiments.

A timing sequence of electrode activation over a series of electrode sets is illustrated in FIG. 8, according to embodiments. Using the example scenario where it is desired to apply a hierarchical ablation waveform to j electrode sets (each electrode set comprising in general at least one anode and at least one cathode, in some embodiments, cardiac pacing is utilized as described in the foregoing, and a packet of pulses (such as including one or more pulse groups, or one or more sets of pulses) is applied first to electrode set 1, and with only a small time delay $t_d$ (of the order of about 100 µs or less) this is followed by the packet of pulses being applied to electrode set 2. Subsequently, with another time delay, the packet of pulses is applied to electrode set 3, and so on to electrode set j. This sequence 632 of applications of the packet of pulses to all the j electrode sets is delivered during a single heartbeat's refractory time window (such as the common refractory time window 66 or 67), and each application to an electrode set constitutes one packet for that electrode set. Consider now the case of a monophasic hierarchical waveform. Referring to the monophasic waveform example shown in FIG. 3, the waveform has a series of monophasic pulses each with pulse width w, separated by a time interval of duration $t_1$ between successive pulses, a number $m_1$ of which are arranged to form a group of pulses. Furthermore, the waveform has a number $m_2$ of such groups of pulses separated by a time interval of duration $t_2$ between successive groups, thereby defining a packet. If this waveform is applied in sequence over the j electrode sets as described here, we can write the inequality $$j[m_2(m_1 w + t_1(m_1-1)) + t_2(m_2-1)] + t_d(j-1) < T_r. \quad (1)$$

that the pulse waveform parameters $m_1$ and $m_2$ must satisfy for a given number of electrode sets j, in order for the entire ablation pulse delivery to occur within a refractory time window $T_r$. In some embodiments, the refractory time window $T_r$ can be about 140 milliseconds or less. The time offset of the start of the refractory window with respect to a pacing signal can be less than about 10 milliseconds. While the time intervals w, $t_1$, $t_2$ and $t_d$ can be arbitrary, when implemented with finite state machines such as (for example) a computer processor, they are integers as measured in some suitable units (such as, for example, microseconds, nanoseconds or multiples of a fundamental processor clock time period). Given a number of electrode sets j, equation (1) represents a Diophantine inequality mutually constraining the pulse waveform parameters (pulse width, time intervals and numbers of pulses and groups) such that the total duration of the waveform application over the j electrode sets is smaller than a given common refractory period. In some embodiments, a solution set for the Diophantine inequality can be found based on partial constraints on the pulse waveform parameters. For example, the generator can require input of some of the pulse waveform parameters and/or related parameters, for example the pulse width w and time delay $t_d$, after which the system console determines the rest of the pulse waveform parameters. In this case the number of electrode sets j is also an input to the system that constrains the solution determination. In one embodiment the system console could display more than one such possible solution set of waveform parameters for the user to make a selection, while in an alternate embodiment the system makes an automatic selection or determination of the waveform parameters. In some embodiments, a solution can be calculated and directly implemented in pre-determined form, such as, for example, on a pulse generator system console. For example, all of the pulse waveform parameters are pre-determined to satisfy a Diophantine inequality similar to equation (1) and the waveform is pre-programmed on the system; possibly the pre-determined solution(s) can depend on the number of electrode sets j, or alternately the solution(s) can be pre-determined assuming a maximal number for the electrode sets. In some embodiments more than one solution could be pre-determined and made available for user selection on the system console.

While the Diophantine inequality (1) holds for delivery of a single waveform packet over a single refractory time window, the full waveform can sometimes involve a plurality of packets. The number of packets can be pre-determined and in one embodiment can range from 1 to 28 packets, including all values and sub ranges in between. The appropriate refractory time window $T_r$ can be pre-determined and/or pre-defined in one embodiment or, in an alternate embodiment, it can be selected by a user from within a certain pre-determined range. While inequality (1) was explicitly written for a monophasic hierarchical waveform, a similar inequality may be written for a biphasic waveform, or for a waveform that combines monophasic and biphasic elements.

A schematic illustration of ablation waveform delivery over multiple electrode sets j with a series of packets at the top level of the waveform hierarchy is provided in FIG. 8. The first waveform packet 632 is delivered over a sequence of j electrode sets in succession over the entire electrode sequence; the waveform parameters for this sequence satisfy a Diophantine inequality such as equation (1). This entire voltage waveform sequence is delivered within a defined refractory time window of a single paced heartbeat. After a packet delay $t_3$ equal to one pacing period, the next waveform packet 633 is delivered over the j electrode sets in succession over the entire electrode sequence with the same waveform parameters. The waveform delivery is continued over the pre-determined number of packets until the last waveform packet 636 is delivered over the j electrode sets in succession. Thus ablation delivery occurs over as many paced heartbeats as there are packets. The voltage amplitude for the waveform can range between approximately 700V and approximately 10,000V, and more preferably between approximately 1,000V and approximately 8,000V, as suitable and convenient for the clinical application, including all values and sub ranges in between.

In some embodiments, the complete sequence of electrode sets can be subdivided into smaller subsequences of electrode sets/electrode subsets. For example, the complete sequence of j electrode sets can be subdivided into N subsequences with $j_1$ electrode sets in the first subsequence/first subset, $j_2$ electrode sets in the second subsequence/second subset, and so on, with $j_N$ electrode sets in the N-th subsequence. The waveform packets are applied first over the first subsequence of $j_1$ electrode sets, then over the second subsequence of $j_2$ electrode sets, and so on, with cardiac pacing employed throughout and all waveform packets applied within appropriate refractory time windows.

Furthermore, waveform delivery over each subsequence of electrode sets may be multiplexed in the manner described herein for increased efficiency and/or speed of ablation delivery, with cliques comprising 1, 2, 3, 4 or more paired electrode subsets as described herein.

While the pulsed waveform delivery is described here as having each packet or second set of pulses be delivered within a signal refractory period of a cardiac cycle, it can be appreciated in other embodiments that parameters (e.g., number of pulses, groups, packets, etc. and durations of time intervals or time delays) can be varied to allow for higher levels of a hierarchy of a pulsed waveform to be delivered within a single refractory period. For example, in an embodiment, a plurality of second sets of pulses (e.g., a super-packet) can be configured to be delivered during a single refractory period, with the number of pulses, groups, packets, etc. and the duration of first, second, etc. time intervals or delays being adjusted to fit all three levels of the hierarchy within a single refractory period.

System

Figure 9:
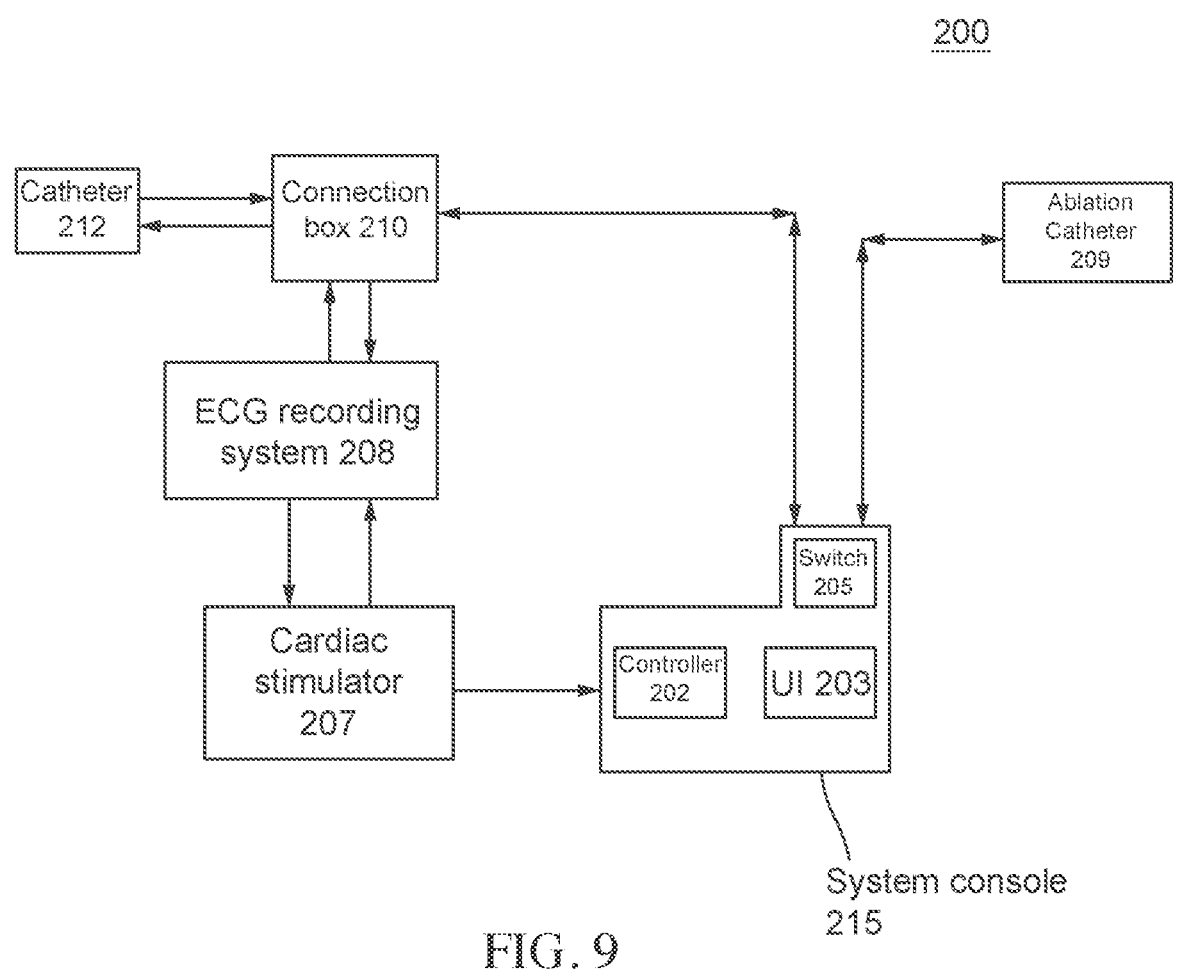
FIG. 9 is a schematic illustration of an irreversible electroporation system that includes a system console that in turn includes a voltage/signal generator, a controller configured to apply voltages to selected subsets of electrodes and that is communicably connected to a computer or processor together with a user interface, and a switching unit configured to electrically isolate other equipment from voltage pulses that may be delivered to an ablation catheter from the voltage generator, according to embodiments.

FIG. 9 is a schematic illustration of a system architecture for an ablation system 200 configured for delivery of pulsed voltage waveforms. The system 200 includes a system console 215, which in turn includes a pulsed waveform generator and controller 202, a user interface 203, and a switch 205 for isolating a connection box 210 (to which multiple catheters may be connected) from voltage pulses delivered by the generator. In some embodiments, the generator/controller 202 can include a processor, which can be any suitable processing device configured to run and/or execute a set of instructions or code. The processor can be, for example, a general purpose processor, a Field Programmable Gate Array (FPGA), an Application Specific Integrated Circuit (ASIC), a Digital Signal Processor (DSP), and/or the like. The processor can be configured to run and/or execute application processes and/or other modules, processes and/or functions associated with the system and/or a network associated therewith (not shown).

In some embodiments, the system 200 can also include a memory and/or a database (not shown) configured for, for example, storing pacing data, waveform information, and/or the like. The memory and/or the database can independently be, for example, a random access memory (RAM), a memory buffer, a hard drive, a database, an erasable programmable read-only memory (EPROM), an electrically erasable read-only memory (EEPROM), a read-only memory (ROM), Flash memory, and/or so forth. The memory and/or the database can store instructions to cause the generator/controller 202 to execute modules, processes and/or functions associated with the system 200, such as pulsed waveform generation and/or cardiac pacing.

The system 200 can be in communication with other devices (not shown) via, for example, one or more networks, each of which can be any type of network such as, for example, a local area network (LAN), a wide area network (WAN), a virtual network, a telecommunications network, and/or the Internet, implemented as a wired network and/or a wireless network. Any or all communications can be secured (e.g., encrypted) or unsecured, as is known in the art. The system 200 can include and/or encompass a personal computer, a server, a work station, a tablet, a mobile device, a cloud computing environment, an application or a module running on any of these platforms, and/or the like.

The system console 215 delivers ablation pulses to an ablation catheter 209 that is suitably positioned in a patient anatomy such as, for example, in a loop around the patient's pulmonary veins in a pericardial space of the patient's heart. An intracardiac ECG recording and pacing catheter 212 is coupled to an ECG recording system 208 via the connection box 210. The ECG recording system 208 is connected to a cardiac stimulator or pacing unit 207. The cardiac stimulator 207 can send a pacing output to the recording and pacing catheter 212; in general both atrial and ventricular pacing signals can be generated as outputs from the cardiac stimulator 207, and in some embodiments there can be separate intracardiac atrial and ventricular pacing catheters (not shown) or leads, each of which can then be disposed and/or positioned in the appropriate cardiac chamber. The same pacing output signal is also sent to the ablation system console 215. The pacing signal is received by the ablation system console and, based on the pacing signal, the ablation waveform can be generated by the generator/controller 202 within a common refractory window as described herein. In some embodiments, the common refractory window can start substantially immediately following the ventricular pacing signal (or after a very small delay) and last for a duration of approximately 250 ms or less thereafter. In this case, the entire ablation waveform packet is delivered within this duration, as explained earlier.

Figure 10:
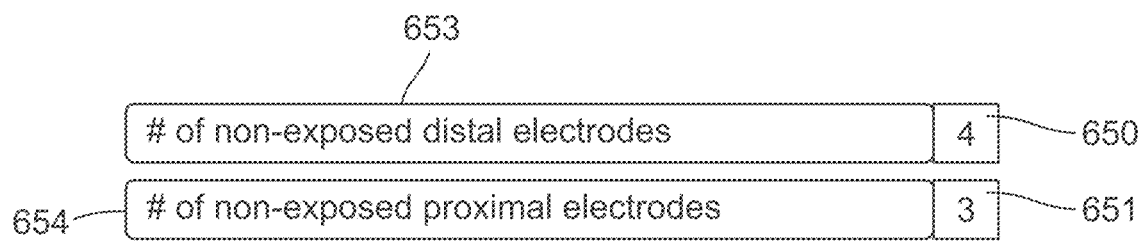
FIG. 10 is a schematic illustration of a user interface in an initial configuration, according to embodiments.

The user interface 203 associated with the ablation system console 215 can be implemented in a variety of forms as convenient for the application. When an epicardial ablation catheter is delivered via a subxiphoid approach and is placed epicardially around the pulmonary veins as shown in FIG. 1, it may be cinched in place at the ends 8 and 9 by passing the ends through a cinch tool. Depending on the size of the specific left atrial anatomy, a subset of the electrodes may be disposed around the pulmonary veins in encircling fashion while a remainder of the electrodes may be pulled inside the cinch tool (not shown in FIG. 1) and thus are not exposed. In such embodiments, the encircling/exposed electrodes can be selectively used for delivering ablation energy. An embodiment of a user interface suitable for use with an ablation catheter is schematically depicted in FIG. 10. In FIG. 10, a user may select the number of proximal electrodes inside the cinch tool and the number of distal electrodes inside the cinch tool as indicated in windows 653 and 654 respectively where the user has made selections 650 and 651 respectively for the respective numbers of electrodes. The complementary electrodes/subset of electrodes on the catheter (taken from the full set of catheter electrodes) that are not inside the cinch tool are the exposed electrodes to be used in the delivery of pulsed electric fields for electroporation ablation. The amplitude of the waveform to be delivered is controlled by an input mechanism such as, for example, the slider 658 that can be moved over a pre-determined voltage range indicated by 657 in FIG. 10. Once a voltage amplitude has been selected, an initialization (or Initialize) button 655 provided on the user interface is engaged to ready the ablation system for energy delivery. In one example, this can take the form of a trigger for charging a capacitor bank to store energy for subsequent delivery to the catheter.

Figure 11:
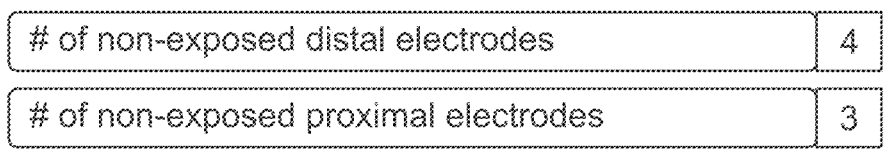
FIG. 11 is a schematic illustration of a user interface showing the engagement of an initialization function, according to embodiments.
Figure 11:
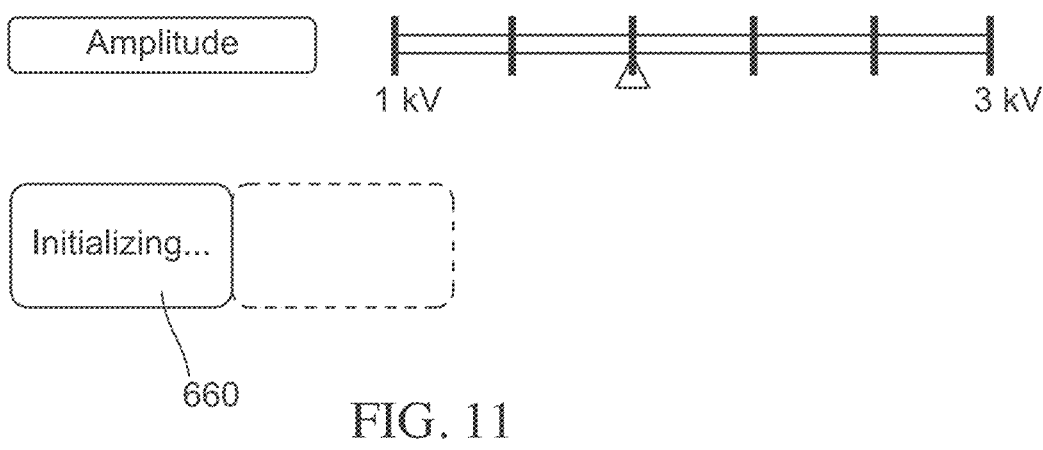
Figure 12:
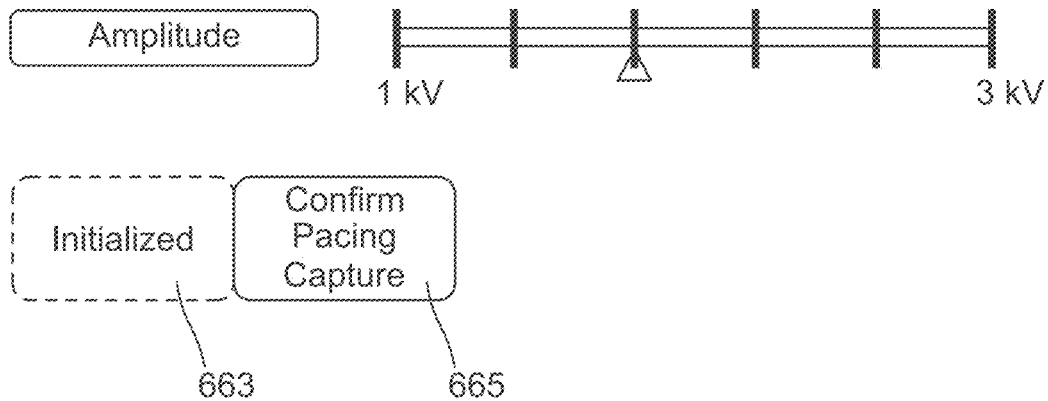
FIG. 12 is a schematic illustration of a user interface showing a required step subsequent to initialization, according to embodiments.

As shown in FIG. 11, the Initialize button 660 can also act as a status indicator that indicates that the initialization process is ongoing. The status can be indicated by text ("Initializing . . . " as shown in FIG. 11, and/or color, such as yellow to indicate that initialization has not yet started or is still in progress). Once the initialization process is complete (e.g., a capacitor bank is fully or satisfactorily charged), as shown in FIG. 12, the same button 663 now indicates completion of the process ("Initialized") and, in some embodiments as illustrated, it can change color (e.g. change from yellow to green) and/or shape to further indicate completion of initialization. Meanwhile, the ablation system awaits reception of a pacing signal from a cardiac stimulator or pacing unit. Once a pacing signal is detected and/or confirmed together with completion of the initialization process, a second button 665 now becomes available for a user to engage, for confirmation of pacing capture. If a pacing signal is not detected by the ablation system console, then the second button 665 is not enabled. The user can monitor an ECG display (not shown) to view the cardiac stimulator pacing output in conjunction with intracardiac ECG recordings in order to confirm pacing capture (this confirms that atrial and ventricular contractions are indeed driven by the pacing signal, in order to establish a predictable common refractory window). Once the user visually confirms pacing capture from the ECG data, (s)he can then engage the "Confirm Pacing Capture" button 665 to confirm pacing capture on the ablation system.

Figure 13:
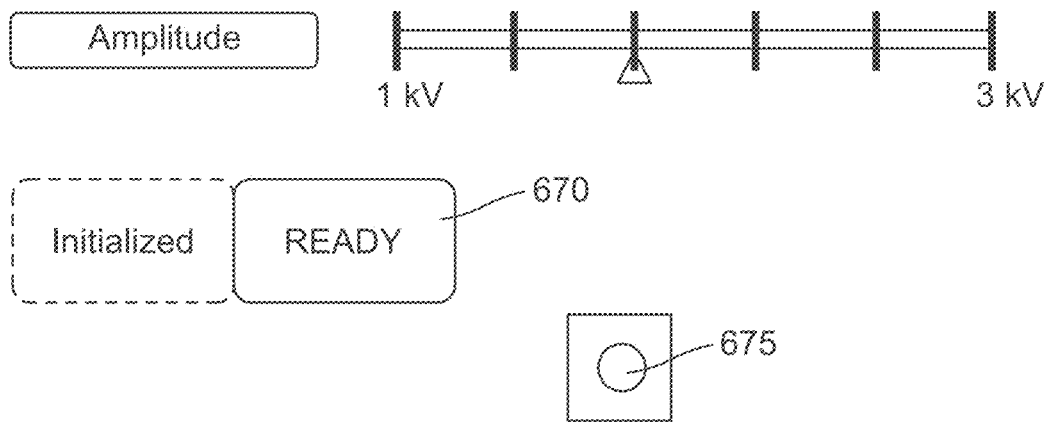
FIG. 13 is a schematic illustration of a user interface showing a configuration where the system is ready, subsequent to the completion of a prior step, for delivery of ablative energy. In this configuration the user interface includes a button for ablation, according to embodiments.

As shown in FIG. 13, once pacing capture is confirmed on the ablation system, the system is now available for ablation or pulsed electric field delivery. The pacing capture confirmation button now changes appearance 670 (the appearance can change in color, shape, and/or the like) and indicates readiness for ablation delivery as shown by 670. Furthermore, an ablation delivery button 675 now becomes available to the user. The user can engage the ablation delivery button 675 to deliver ablation in synchrony with the paced heart rhythm. In some embodiments, the user engages the button 675 for the duration of ablation delivery, at the end of which the button changes shape or color to indicate completion of ablation delivery. In some embodiments, if the user disengages from the button 675 before ablation delivery is completed, ablation delivery is immediately stopped with only a small time lag of no more than, for example, 20 ms. In some embodiments, if the user has not engaged the ablation button 675 after it is displayed as being available, it stays available for engagement for only a limited time duration before it is disabled, as a safety mechanism. In some embodiments the ablation button 675 can be a software or graphic button on a user interface display, while in another embodiment it could be a mechanical button whose response depends on its state of activation or availability as determined by the system, or in another embodiment, the button 675 can be without limitation in the form of any of a variety of control input devices such as a lever, joystick, computer mouse, and so on. In one embodiment, the ablation system can have a separate emergency-stop button for additional safety, for example if it is desired to instantly de-activate the system. In one embodiment, the ablation console can be mounted on a rolling trolley or wheeled cart, and the user can control the system using a touchscreen interface that is in the sterile field. The touchscreen can be for example an LCD touchscreen in a plastic housing mountable to a standard medical rail or post and the touchscreen can have at a minimum the functionality described in the foregoing. The interface can for example be covered with a clear sterile plastic drape.

The waveform parameters as detailed herein can be determined by the design of the signal generator, and in some embodiments the parameters can be pre-determined. In some embodiments, at least a subset of the waveform parameters could be determined by user control as may be convenient for a given clinical application. The specific examples and descriptions herein are exemplary in nature and variations can be developed by those skilled in the art based on the material taught herein without departing from the scope of embodiments disclosed herein.

One or more embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code disclosed herein.

One or more embodiments and/or methods described herein can be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) can be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

While illustrative epicardial catheters are discussed as examples herein, it should be understood that endocardial catheters and other medical devices comprising multiple electrodes for delivery of Pulsed Electric Field (PEF) energy and tissue ablation may benefit from the multiplexing and interleaving disclosed herein for efficient electrode sequencing and PEF ablation delivery. In some embodiments, the methods, systems, and devices disclosed herein may comprise one or more of the methods, systems, and devices described in one or more of International Application Ser. No. PCT/US2018/29938, filed on Apr. 27, 2018, the contents of which are hereby incorporated by reference in its entirety.

While various embodiments have been described above, it should be understood that they have been presented by way of example, and not limitation. Where methods described above indicate certain events occurring in certain order, the ordering of certain events can be modified. Additionally, certain of the events may be performed concurrently in a parallel process when possible, as well as performed sequentially as described above.

What is claimed is:

1. A system, comprising:
    a pulse waveform generator operatively coupled to an ablation device, the pulse waveform generator configured to:
        select a plurality of electrode sets from a plurality of electrodes of the ablation device, each electrode set from the plurality of electrode sets including a first subset of electrodes configured as one or more anodes and a second subset of electrodes configured as one or more cathodes;
        generate voltage pulses in the form of pulsed waveforms, each pulsed waveform including:
            (a) a first level of a hierarchy of the pulsed waveform that includes a first set of pulses and a first time delay separating successive pulses of the first set of pulses;
            (b) a second level of the hierarchy of the pulsed waveform that includes a plurality of first sets of pulses as a second set of pulses and a second time delay separating successive first sets of pulses, the second time delay being greater than the first time delay; and
            (c) a third level of the hierarchy of the pulsed waveform that includes a plurality of second sets of pulses as a third set of pulses and a third time delay separating successive second sets of pulses, the third time delay being greater than the second time delay; and
        deliver the voltage pulses to the plurality of electrode sets according to a predefined sequence with at least one pulsed waveform being applied across the first and second subsets of electrodes of each electrode set from the plurality of electrode sets.

2. The system of claim 1, wherein each pulse of each first set of pulses includes biphasic pulses.

3. The system of claim 2, wherein a voltage amplitude of each biphasic pulse is at least about 500 Volts, and a pulse time duration of each biphasic pulse is between about 0.5 nanoseconds and about 20 microseconds.

4. The system of claim 1, wherein the pulse waveform generator is configured to deliver the voltage pulses in synchrony with cardiac cycles of a heart of a patient such that successive second sets of pulses of the plurality of second sets of pulses are delivered during refractory periods of distinct cardiac cycles of the heart, and with a delivery window of the third set of pulses extending across a plurality of cardiac cycles of the heart.

5. The system of claim 1, wherein the first time delay is greater than a pulse time duration of each pulse of the first set of pulses.

6. The system of claim 1, wherein the second time delay is at least twenty times the duration of the first time delay.

7. The system of claim 1, wherein each second set of pulses includes at least two first sets of pulses and less than forty first sets of pulses.

8. The system of claim 1, wherein the pulse waveform generator is configured to deliver the voltage pulses to the plurality of electrode sets with voltage pulses delivered to a first electrode set from the plurality of electrode sets being offset by a period of time from voltage pulses delivered to a second electrode set from the plurality of electrode sets.

9. The system of claim 8, wherein the period of time offsetting the delivery of voltage pulses to the first electrode set and the delivery of voltage pulses to the second electrode set is less than the second time delay.

10. The system of claim 1, wherein each pulsed waveform further includes a fourth level of the hierarchy that includes a plurality of third sets of pulses as a fourth set of pulses and fourth time delays separating successive third sets of pulses of the plurality of third sets of pulses, each fourth time delay being greater than the third time delay.

11. A method, comprising:
    selecting a plurality of electrode sets from a plurality of electrodes of an ablation device, each electrode set including a first subset of electrodes configured to be anodes and a second subset of electrodes configured to be cathodes;

generating voltage pulses in the form of pulsed waveforms, each pulsed waveform including:
(a) a first level of a hierarchy of the pulsed waveform that includes a first set of pulses and a first time delay separating successive pulses of the first set of pulses;
(b) a second level of the hierarchy of the pulsed waveform that includes a plurality of first sets of pulses as a second set of pulses and a second time delay separating successive first sets of pulses, the second time delay being greater than the first time delay; and
(c) a third level of the hierarchy of the pulsed waveform that includes a plurality of second sets of pulses as a third set of pulses and a third time delay separating successive second sets of pulses, the third time delay being greater than the second time delay; and
delivering the voltage pulses to the plurality of electrode sets according to a predefined sequence with at least one pulsed waveform being applied across the first and second subsets of electrodes of each electrode set from the plurality of electrode sets.

12. The method of claim 11, wherein the voltage pulses are delivered in synchrony with cardiac cycles of the heart such that successive second sets of pulses of the plurality of second sets of pulses are delivered during refractory periods of distinct cardiac cycles of a heart of a patient, and with a delivery window of the third set of pulses extending across a plurality of cardiac cycles of the heart.

13. The method of claim 12, wherein the period of time offsetting the delivery of voltage pulses to the first electrode set and the delivery of voltage pulses to the second electrode set is less than the second time delay.

14. The method of claim 11, wherein the voltage pulses are delivered to a first electrode set from the plurality of electrode sets offset by a period of time from delivering the voltage pulses to a second electrode set from the plurality of electrode sets.

15. The method of claim 11, wherein each pulsed waveform further includes a fourth level of the hierarchy that includes a plurality of third sets of pulses as a fourth set of pulses and fourth time delays separating successive third sets of pulses of the plurality of third sets of pulses, each fourth time delay being greater than the third time delay.

16. The method of claim 11, wherein the second time delay is at least twenty times the duration of the first time delay.

17. A system, comprising:
a pulse waveform generator operatively coupled to an ablation device, the pulse waveform generator configured to:
select electrode sets from a plurality of electrodes of the ablation device, each electrode set from the plurality of electrode sets including a first subset of electrodes configured as one or more anodes and a second subset of electrodes configured as one or more cathodes;
generate voltage pulses in the form of pulsed waveforms, each pulsed waveform including:
(a) a first level of a hierarchy of the pulsed waveform that includes a first set of pulses and a first time delay separating successive pulses of the first set of pulses; and
(b) a second level of the hierarchy of the pulsed waveform that includes a plurality of first sets of pulses as a second set of pulses and a second time delay separating successive first sets of pulses, the second time delay being greater than the first time delay; and
deliver the voltage pulses to the plurality of electrode sets by:
delivering the plurality of first sets of pulses of a first pulse waveform to a first electrode set from the plurality of electrode sets; and
delivering, (1) subsequent to delivering each first set of pulses of the first pulse waveform and (2) during the second time delay separating that first set of pulses from a successive first set of pulses of the first pulse waveform, the first set of pulses of one or more additional pulse waveforms to one or more additional electrode sets from the plurality of electrode sets according to a predefined sequence, such that successive first sets of pulses delivered to the one or more additional electrode sets follow successive first sets of pulses delivered to the first electrode set.

18. The system of claim 17, wherein each pulse of each first set of pulses includes biphasic pulses.

19. The system of claim 17, wherein a voltage amplitude of each biphasic pulse is at least about 500 Volts, and a pulse time duration of each biphasic pulse is between about 0.5 nanoseconds and about 20 microseconds.

20. The system of claim 17, wherein the pulse waveform generator is configured to deliver the voltage pulses in synchrony with cardiac cycles of the heart such that successive second sets of pulses of the plurality of second sets of pulses are delivered during refractory periods of distinct cardiac cycles of the heart.

21. The system of claim 17, wherein the first time delay is greater than a pulse time duration of each pulse of the first set of pulses.

22. The system of claim 17, wherein the second time delay is at least twenty times the duration of the first time delay.

23. The system of claim 17, wherein each second set of pulses includes at least two first sets of pulses and less than forty first sets of pulses.

24. The system of claim 17, wherein each pulsed waveform further includes a third level of the hierarchy of the pulsed waveform that includes a plurality of second sets of pulses as a third set of pulses and a third time delay separating successive second sets of pulses, the third time delay being greater than the second time delay.

25. A method, comprising:
selecting a plurality of electrode sets from a plurality of electrodes of an ablation device, each electrode set including a first subset of electrodes configured to be anodes and a second subset of electrodes configured to be cathodes;
generating voltage pulses in the form of pulsed waveforms, each pulsed waveform including:
(a) a first level of a hierarchy of the pulsed waveform that includes a first set of pulses and a first time delay separating successive pulses of the first set of pulses; and
(b) a second level of the hierarchy of the pulsed waveform that includes a plurality of first sets of pulses as a second set of pulses and a second time delay separating successive first sets of pulses, the second time delay being greater than the first time delay; and delivering the voltage pulses to the plurality of electrode sets by:
- delivering the plurality of first sets of pulses of a first pulse waveform to a first electrode set from the plurality of electrode sets; and
- delivering, (1) subsequent to delivering each first set of pulses of the first pulse waveform and (2) during the second time delay separating that first set of pulses from a successive first set of pulses of the first pulse waveform, the first set of pulses of one or more additional pulse waveforms to one or more additional electrode sets from the plurality of electrode sets according to a predefined sequence, such that successive first sets of pulses delivered to the one or more additional electrode sets follow successive first sets of pulses delivered to the first electrode set.

26. The method of claim 25, wherein the second time delay is at least twenty times the duration of the first time delay.

27. The method of claim 25, wherein the voltage pulses are delivered in synchrony with cardiac cycles of the heart such that successive second sets of pulses of the plurality of second sets of pulses are delivered during refractory periods of distinct cardiac cycles of the heart.

28. The method of claim 25, wherein each pulsed waveform further includes a third level of the hierarchy of the pulsed waveform that includes a plurality of second sets of pulses as a third set of pulses and a third time delay separating successive second sets of pulses, the third time delay being greater than the second time delay.

* * * * *